United States Patent
Short

(10) Patent No.: US 11,396,717 B2
(45) Date of Patent: Jul. 26, 2022

(54) COMPREHENSIVE MONOCLONAL ANTIBODY GENERATION

(71) Applicant: BioAtla, Inc., San Diego, CA (US)

(72) Inventor: Jay M. Short, Del Mar, CA (US)

(73) Assignee: BioAtla, Inc., San Diego, CA (US)

( * ) Notice: Subject to any disclaimer, the term of this patent is extended or adjusted under 35 U.S.C. 154(b) by 109 days.

(21) Appl. No.: 16/859,150

(22) Filed: Apr. 27, 2020

(65) Prior Publication Data

US 2020/0256875 A1 Aug. 13, 2020

Related U.S. Application Data

(62) Division of application No. 13/977,193, filed as application No. PCT/US2011/067596 on Dec. 28, 2011, now Pat. No. 10,670,608.

(60) Provisional application No. 61/429,004, filed on Dec. 31, 2010, provisional application No. 61/429,690, filed on Jan. 4, 2011.

(51) Int. Cl.
| | |
|---|---|
| C40B 30/04 | (2006.01) |
| C07K 16/00 | (2006.01) |
| G01N 33/50 | (2006.01) |
| G01N 33/577 | (2006.01) |
| G01N 33/68 | (2006.01) |

(52) U.S. Cl.
CPC .............. *C40B 30/04* (2013.01); *C07K 16/00* (2013.01); *C07K 16/005* (2013.01); *G01N 33/5052* (2013.01); *G01N 33/577* (2013.01); *G01N 33/6857* (2013.01); *C07K 2317/56* (2013.01)

(58) Field of Classification Search
None
See application file for complete search history.

(56) References Cited

U.S. PATENT DOCUMENTS

| | | |
|---|---|---|
| 6,331,415 B1 | 12/2001 | Cabilly et al. |
| 7,858,559 B2 | 12/2010 | Zauderer et al. |
| 2005/0043516 A1 | 2/2005 | Chuntharapai et al. |
| 2005/0123900 A1 | 6/2005 | Demitrov et al. |

(Continued)

FOREIGN PATENT DOCUMENTS

| | | |
|---|---|---|
| AU | 561199 A1 | 12/1999 |
| GB | 2461546 A | 1/2010 |
| KR | 10-2005-0116360 A | 12/2005 |

(Continued)

OTHER PUBLICATIONS

Mutharia, Lucy M., et al. "Monoclonal antibodies specific for *Escherichia coli* J5 lipopolysaccharide: cross-reaction with other gram-negative bacterial species." Infection and Immunity 45.3 (1984): 631-636.

(Continued)

*Primary Examiner* — Christian C Boesen
(74) *Attorney, Agent, or Firm* — Mendelsohn Dunleavy, P.C.

(57) ABSTRACT

The present invention relates to methods for efficiently generating recombinant monoclonal antibodies derived from B cells of a non-human host which has been immunochallenged with one or more target antigens. The methods comprise the steps of identifying and isolating B cell that bind to the antigen by FACS, and recombining and enriching for thousands of cells to create a B cell library. Related products and methods, such as methods of producing expression libraries, are also disclosed.

31 Claims, 4 Drawing Sheets

(56) References Cited

U.S. PATENT DOCUMENTS

| | | |
|---|---|---|
| 2005/0255532 A1 | 11/2005 | Ruben et al. |
| 2007/0258954 A1 | 11/2007 | Iverson et al. |

FOREIGN PATENT DOCUMENTS

| | | |
|---|---|---|
| WO | 9318068 A1 | 9/1993 |
| WO | 9411507 A2 | 5/1994 |
| WO | WO2008076487 A2 | 6/2008 |
| WO | WO2010001251 A2 | 1/2010 |

OTHER PUBLICATIONS

Extended European Search Report for corresponding European application No. 21193997.0; dated Jan. 31, 2022 (17 pages).

International Search Report and Written Opinion for PCT/US11/67596; dated Apr. 24, 2014.

European Search Report; dated Apr. 23, 2014 for the related EP Application No. 11852493.3.

Yanisch-Perron et al. "Improved M13 phage cloning vectors and host strains: nucleotide sequences of the M13mp18 and pUC19 vectors" Gene 33.1 (1985): pp. 103-119.

Brekke et al. "Therapeutic antibodies for human diseases at the down of the twenty-first century" Nature Reviews Drug Discovery 2.1 (2003): pp. 52-62.

Altshuler et al. "Generation of Recombinant Antibodies and Means for Increasing Their Affinity" Biochemistry (Moscow) 75.13: pp. 1584-15605.

Nguuyen et al. "The Specific Variable Domain of Camel Heavy-chain Antibodies is Encoded in the Germline" Journal of Molecular Biology 275.3 (1998): pp. 413-418.

Glanville et al. "Precise determination of the diversity of combinatorial antibody library gives insight into the human immunoglobulin repertoire" Proceedings of the National Academy of Sciences 106.48 (2009): pp. 20216-20221.

Kramer "Synthesis of a group-selective antibody library against haptens" Journal of Immunological Methods 266.1-2 (2002): pp. 209-220.

Kramer et al. "Molecular Antibody Technologies for Biosensors and Bioanalytics" Handbook of Biosensors and Biochips Two (2008): pp. 6.

Shendure et al. "Next-generation DNA sequencing" Nature Biotechnology 26.10 (2008): pp. 1135-1145.

Hawkins et al. "Cell selection strategies for making antibodies from variable gene libraries: trapping the memory pool" European Journal of Immunology 22.3 (1992): pp. 867-870.

Crameri et al. "Construction and evolution of antibody-phage libraries by DNA shuffling" Nature Medicine 2.1 (1996): pp. 100-102.

Chinese Office Action; dated Nov. 13, 2014 for CN Application No. CN 2011800068870.7 along with English abstract.

Chinese Office Action; dated Jul. 16, 2015 for CN Application No. CN 2011800068870.7 along with English abstract.

European Office Action; dated Jun. 24, 2015 for EP Application No. EP 11852493.3.

Canadian Office Action; dated Dec. 20, 2016 for CA Application No. 2,822,969.

AU Examination Report; dated Mar. 17, 2017 for AU Application No. AU 2016203162.

Chinese Office Action; dated Dec. 19, 2018 for CN Application No. 201610287362.2.

Official Action for corresponding Canadian application No. 2,997,473; dated Jan. 11, 2021 (5 pages).

Examination Report No. 1 for corresponding Australian application No. 2019203170; dated Jun. 18, 2020 (4 pages).

Official Action for corresponding Canadian application No. 2,997,473; dated Jul. 2, 2021 (4 pages).

COMPREHENSIVE MONOCLONAL ANTIBODY GENERATION

BACKGROUND OF THE INVENTION

The immune system of a mammal is one of the most versatile biological systems as probably greater than $1 \times 10^7$ antibody specificities can be produced. In an individual animal there are at least 5,000-10,000 different B-cell clones capable of generating unique antibodies. Further, because of the process of somatic mutation during the generation of antibody diversity, essentially an unlimited number of unique antibody molecules may be generated. Indeed, much of contemporary biological and medical research is directed toward tapping this repertoire. The development of the hybridoma methodology by Kohler and Milstein made it possible to produce monoclonal antibodies, i.e., a composition of antibody molecules of a single specificity, from the repertoire of antibodies induced during an immune response.

Unfortunately, current methods for generating monoclonal antibodies are not capable of efficiently surveying the entire antibody response induced by a particular immunogen. In contrast to this vast potential for different antibodies, current hybridoma methodologies typically yield only a few hundred different monoclonal antibodies per fusion.

Other difficulties in producing monoclonal antibodies with the hybridoma methodology include genetic instability and low production capacity of hybridoma cultures. One means by which the art has attempted to overcome these latter two problems has been to clone the immunoglobulin-producing genes from a particular hybridoma of interest into an expression system.

Analysis of antibodies expressed at a given moment in a subject is not trivial, since the immunoglobulin repertoire probably contains millions of different molecules. Only a small number of reagents capable of specifically recognizing elements of such a repertoire are currently available. Determining the sequence of expressed genes is possible; however, practically speaking, it is difficult to analyze routinely more than about ten or, perhaps, a hundred genes, and the operation is expensive and time-consuming. In short, the repertoire of immunoglobulins is described at the present time only by a small number of means.

The present invention provides methods to efficiently produce high-affinity monoclonal antibodies taking advantage of natural diversity and high diversity approaches.

SUMMARY OF THE INVENTION

In one embodiment, the invention provides a method of generating and identifying a recombinant antibody that binds at least one target antigen comprising screening B cells to generate a B cell library enriched in B cells capable of binding to the at least one target antigen; amplifying cDNA obtained from mRNA expressed in the B cell library to prepare an immunoglobulin library comprising $V_H$ and $V_L$ domains; generating antibodies from the $V_H$ and $V_L$ domains whereby the antibodies comprise light chain/heavy chain combinations and whereby the number of combinations generated is more than the number of B cells in the enriched B cell library; and screening the antibodies with the at least one target antigen to identify a subset of antibodies capable of binding to the at least one target antigen; whereby a recombinant antibody that binds at least one target antigen is generated and identified.

In another embodiment, the invention also provides a method of generating and identifying a recombinant antibody that binds at least one target antigen comprising screening a population of B cells to generate a B cell library enriched in B cells capable of binding to the at least one target antigen; amplifying cDNA obtained from mRNA expressed in a single B cell for a plurality of B cells in the B cell library to prepare an immunoglobulin library comprising $V_H$ and $V_L$ domains; cloning the immunoglobulin library into an expression vector to form a library of expression vectors capable of expressing the $V_H$ and $V_L$ domains, whereby the $V_H$ and $V_L$ domains are naturally paired; and using the library of expression vectors to express the $V_H$ and $V_L$ domains in an expression system to form an antibody library, wherein the antibodies comprise naturally paired $V_H$ and $V_L$ domains; screening the antibody library for binding to the at least one target antigen.

In another embodiment, the invention provides a method of generating and identifying a recombinant antibody that binds at least one target antigen comprising screening B cells to generate a B cell library enriched in B cells capable of binding to the at least one target antigen; amplifying cDNA obtained from mRNA expressed in the B cell library to prepare an immunoglobulin library comprising $V_H$ domains; generating antibodies from the $V_H$ domains and at least one $V_L$ domain from another source, whereby the antibodies comprise light chain/heavy chain combinations; and screening the antibodies with the at least one target antigen to identify a subset of antibodies capable of binding to the at least one target antigen.

In some embodiments, the B cell library contains at least $10^3$ B cells to at least $10^8$ B cells, including at least $10^3$ B cells, $10^5$ B cells, $10^6$ B cells, $10^7$ B cells or $10^8$ B cells.

In some embodiments, the first screening is selected from the group consisting of fluorescence activated cell sorting (FACS) and panning.

In some embodiments, the at least one target antigen is a single target antigen.

In some embodiments, the at least one target antigen is at least two target antigens and the first screening step is screening for B cells capable of binding to the at least two target antigens. The at least two target antigens can be two epitopes on a single target molecule.

In some embodiments, the B cells are B cells from a non-human host. The non-human host may be immunized with a target antigen. The non-human host may be a rabbit or mouse.

In some embodiments, the antibodies generated are full length antibodies. In other embodiments they are antibody fragments, antibody derivatives, fusion proteins, or chimerized antibodies. The chimerized antibodies may comprise a human Fc.

In some embodiments, the B cells are B cells from a human donor.

In some embodiments, the generating is generating using a biological display system to obtain a cell population displaying the antibodies.

In some embodiments, the second step of screening is the cell population via fluorescence activated cell sorting (FACS).

The biological display system may be a mammalian cell surface display system, yeast cell surface display system, or a bacterial cell surface display system.

In some embodiments, the antibodies generated are full length antibodies.

In some embodiments, the method further comprises obtaining the DNA sequence encoding $V_H$ and $V_L$ domains after generating the antibodies, after screening the antibodies, or both.

Obtaining the DNA sequence encoding $V_H$ and $V_L$ domains includes high-throughput sequencing, deep sequencing or combinations of the two.

In some embodiments, wherein the screening step(s) is(are) high-throughput screening. The high-throughput screening may be FACS or screening an array.

In some embodiment, method further comprises characterizing the antibodies capable of binding to the at least one target antigen.

In some embodiments, the characterizing comprises performing a binding assay to determine binding affinity to the target antigen. The binding assay may be an ELISA. The binding affinity to the target antigen may be between 10 µM and 1 nM, including a binding affinity greater than 10 µM, greater than 100 nM, and greater than 10 nM. Additionally, the binding affinity may be greater than 1 nM.

In some embodiments, the characterizing comprises determining isoelectric point, determining thermal stability, determining sedimentation rate, determining folding rate, determining neutralization of antigen activity, determining antagonistic activity, determining agonistic activity, determining expression level, determining non-specific binding, determining specificity, and determining inhibition of enzymatic activity, determining rigidity/flexibility, determining shape, determining charge, determining stability in different pH, determining stability in different solvents, determining UV stability, determining stability in different mechanical conditions, determining stability in different sonic conditions, determining half life, and/or determining glycosylation.

In some embodiments, the method further comprises evolving the recombinant antibody.

The evolving can be Comprehensive Positional Evolution, Comprehensive Positional Evolution followed by Comprehensive Protein Synthesis, random mutagenesis, and/or PCR shuffling.

In some embodiments, the selection, evolution and expression of the antibody is in a eukaryotic cell production host; and the method comprises generating an anti-antigen antibody library in a eukaryotic cell production host; screening the library for at least one predetermined property, characteristic or activity; selecting a template antibody from the library; evolving the template antibody to produce a set of mutant antibodies in the eukaryotic cell production host with antibody cell surface display; screening the mutant antibodies for the at least one predetermined property, characteristic or activity; selecting an up-mutant antibody from the set of mutant antibodies based upon optimization of the at least one predetermined property, characteristic or activity when compared to the template antibody; and expressing the up-mutant antibody in the same eukaryotic cell production host as in the generating step. In this embodiment, the generating may be generating via cell surface display. In some embodiments, the method further comprises humanizing the recombinant antibody.

In some embodiments, the method comprises screening, via high-throughput screening, optionally comprising fluorescence activated cell sorting (FACS) or robotics, isolated B cells from a non-human host immunized with a target antigen to generate a B cell library enriched in B cells capable of binding to the target antigen; amplifying cDNA obtained from mRNA expressed in the B cell library to prepare an immunoglobulin library comprising $V_H$ and $V_L$ domains; generating a library of full-length antibodies from the $V_H$ and $V_L$ domains using a biological display system to obtain a cell population displaying the antibodies, whereby the antibodies comprise light chain/heavy chain combinations and whereby the number of combinations generated is more than the number of B cells in the enriched B cell library; and screening via high-throughput screening, optionally comprising fluorescence activated cell sorting (FACS) or robotics, the cell population with the target antigen to identify a subset of cells displaying antibodies capable of binding to the target antigen; whereby a recombinant antibody that binds to a target antigen is generated and identified.

DEFINITION OF TERMS

Figure 1:
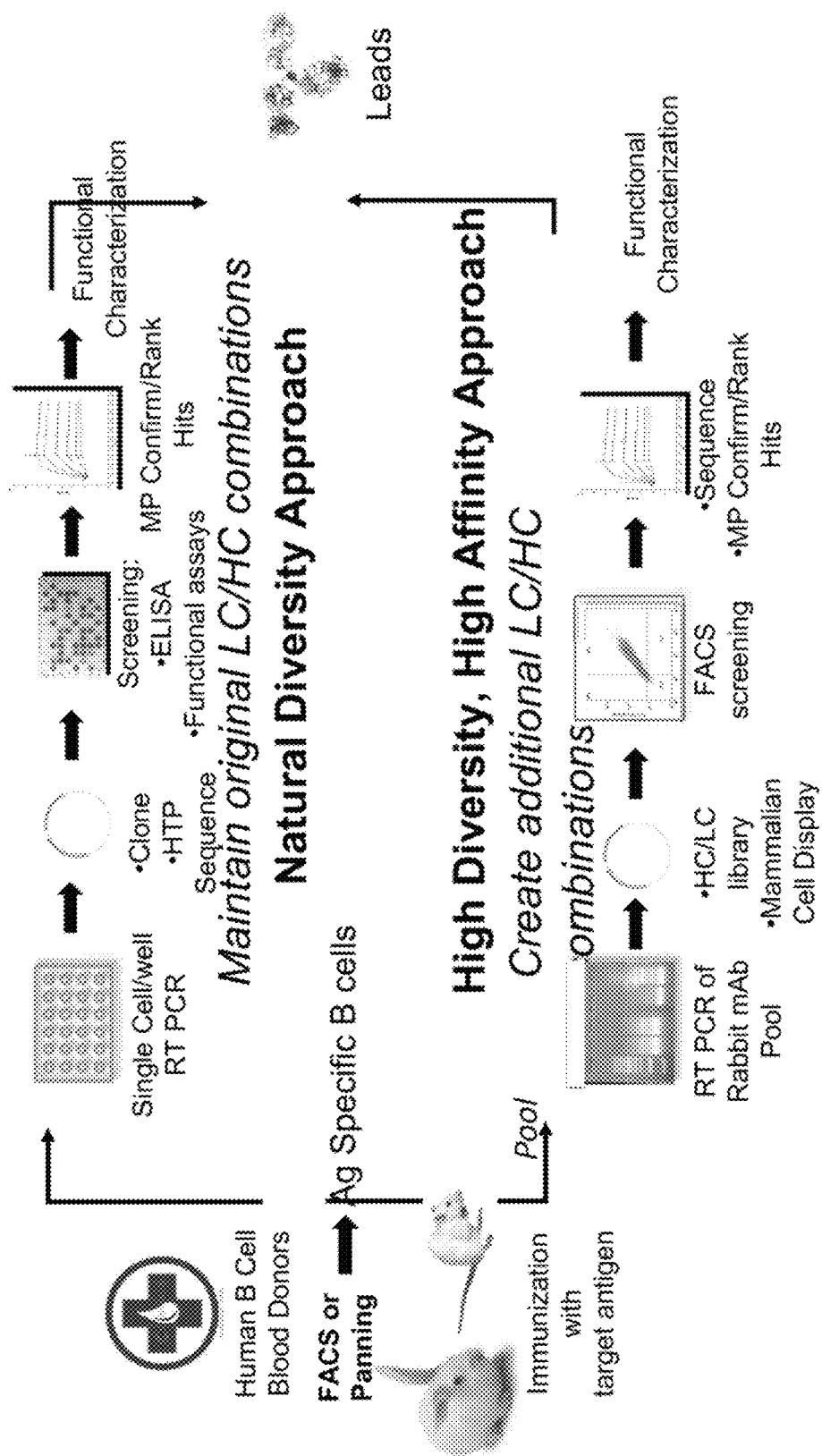
FIG. 1 shows embodiments of the invention for the production of one or more recombinant monoclonal antibodies from B cell libraries. a non-human host is immunized with a target antigen in order to raise antibodies to the target antigen. Alternatively, B cells can be obtained from human B cell blood donors, or transgenic animals that have been engineered with human immune systems. B cells obtained from the host are subjected to screening, such as FACS screening, and B cells that bind the target antigen are isolated to provide a B cell library enriched in B cells that bind to the target antigen. In one embodiment, termed the "natural diversity" approach, PCR is performed on B cells from the library in a manner that maintains original heavy and light chain combinations. For example, RT-PCR is performed on individual B cells from the library with maintenance of the original heavy and light chain combinations from each cell. The resulting nucleic acids are cloned, preferably into a cell surface display system. The resulting library is then screened, for example by ELISA, functional assays or sequencing, including high throughput, deep sequencing. Hits can be confirmed and ranked, if desired. Functional characterization can then be performed on any or all of the hits. In another embodiment, termed the "high diversity" approach, the B cell library is pooled and PCR, such as RT-PCR, is performed on the pooled cells to amplify heavy chain and light chain nucleic acids. These nucleic acids can be sequenced optionally, for example to confirm sequence diversity. In this embodiment, the heavy and light chains are then combined combinatorially at cloning to create a diverse library of heavy/light chain combination molecules. Preferably, the nucleic acids are cloned into a cell surface display system. The resulting library is then screened, for example by ELISA, functional assays or sequencing, including high throughput, deep sequencing. Hits can be confirmed and ranked if desired. Functional characterization can then be performed on any or all of the hits.
Figure 2A:
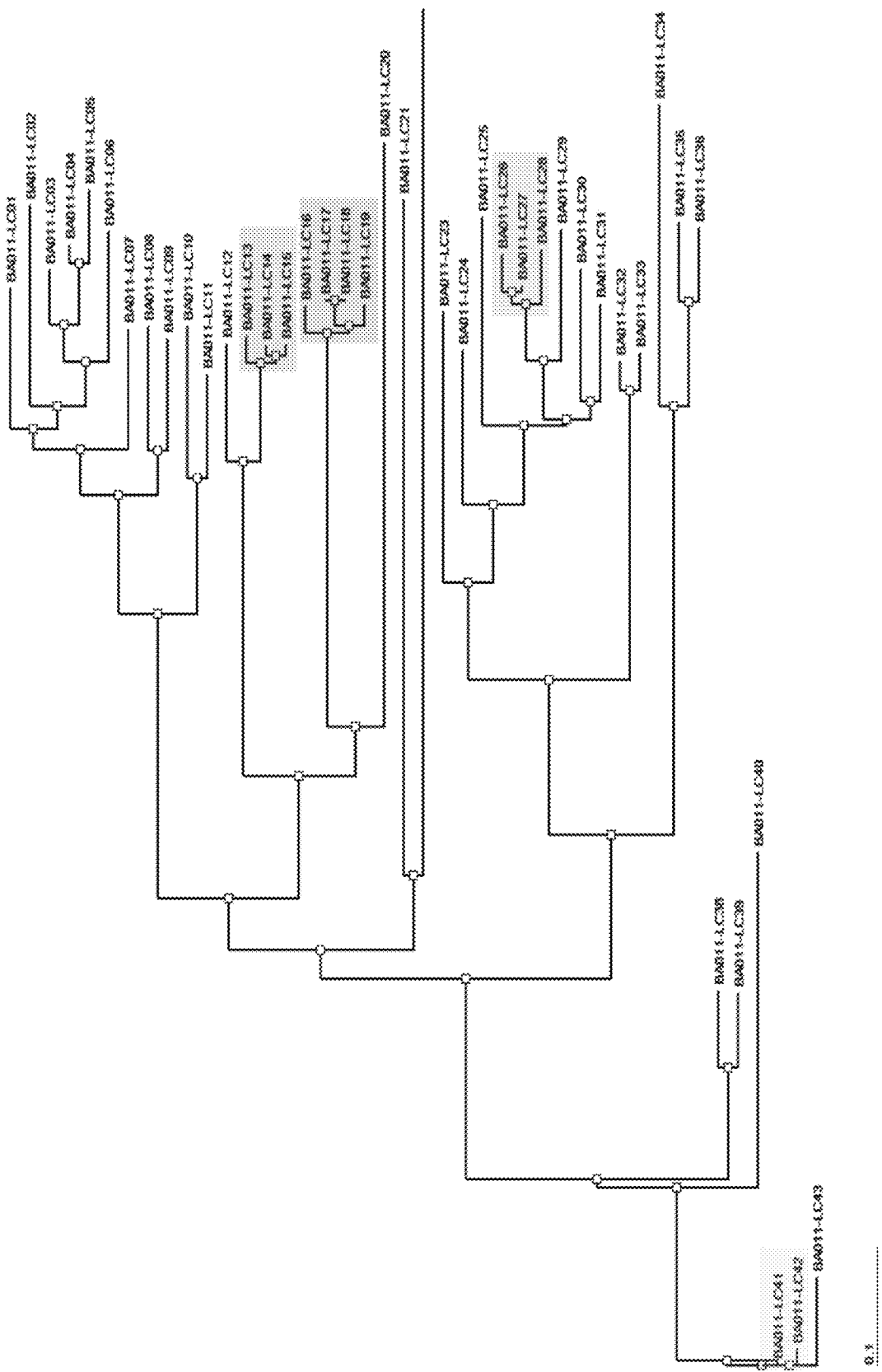
FIGS. 2A and 2B depicts a homology tree of sequences derived from a chimeric library made using the methods of the present invention. Heavy chain and light chain sequences were amplified from B cells derived from an immunized mouse according to the present invention. Sequencing of 15,000 heavy chains and 15,000 light chains followed by comparison shows high diversity of the derivative clones. The data further suggests that the molecules are subject to hyper somatic mutation. The highlighted sequences indicate affinity matured clones.
Figure 2B:
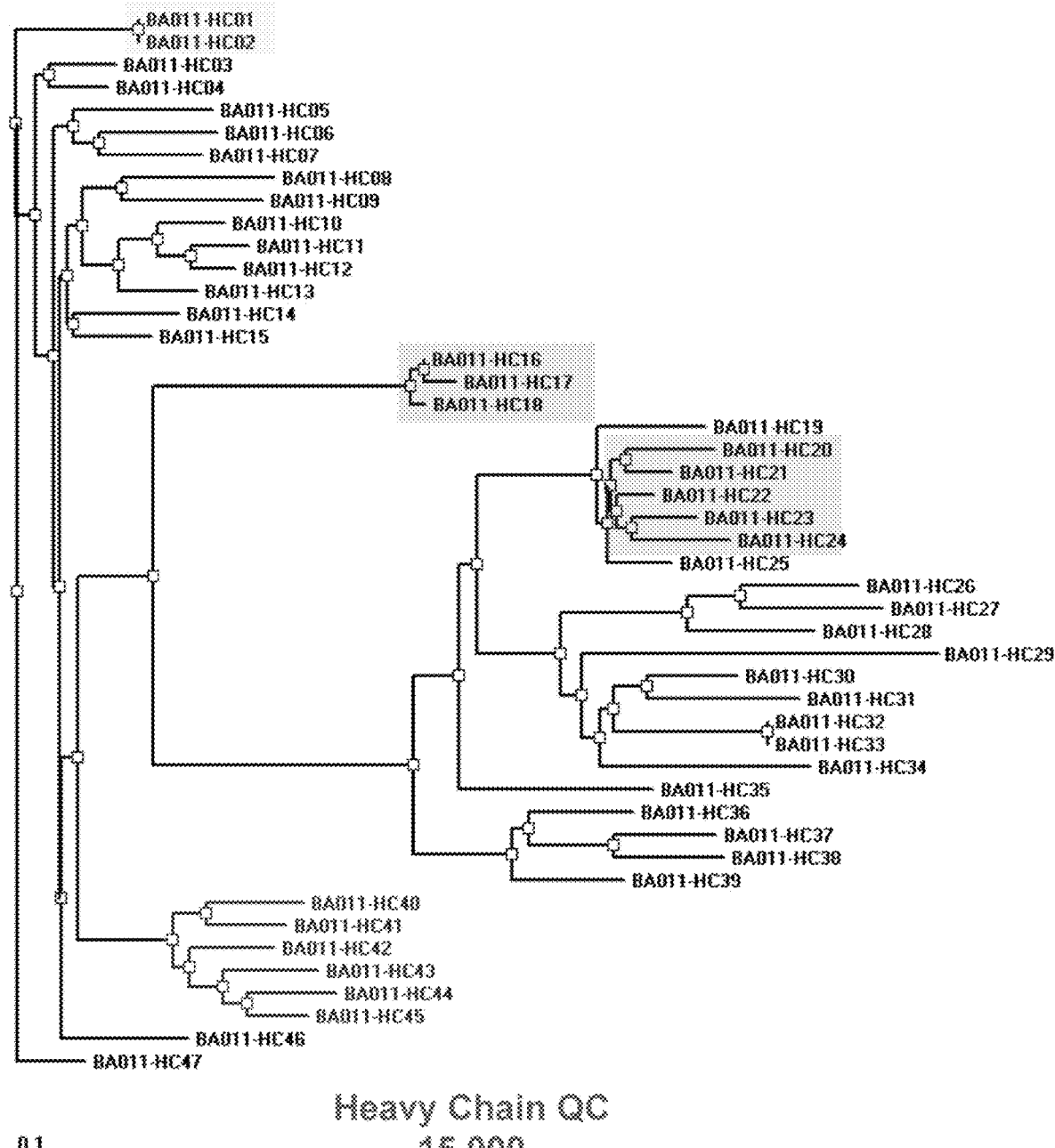
Figure 3:
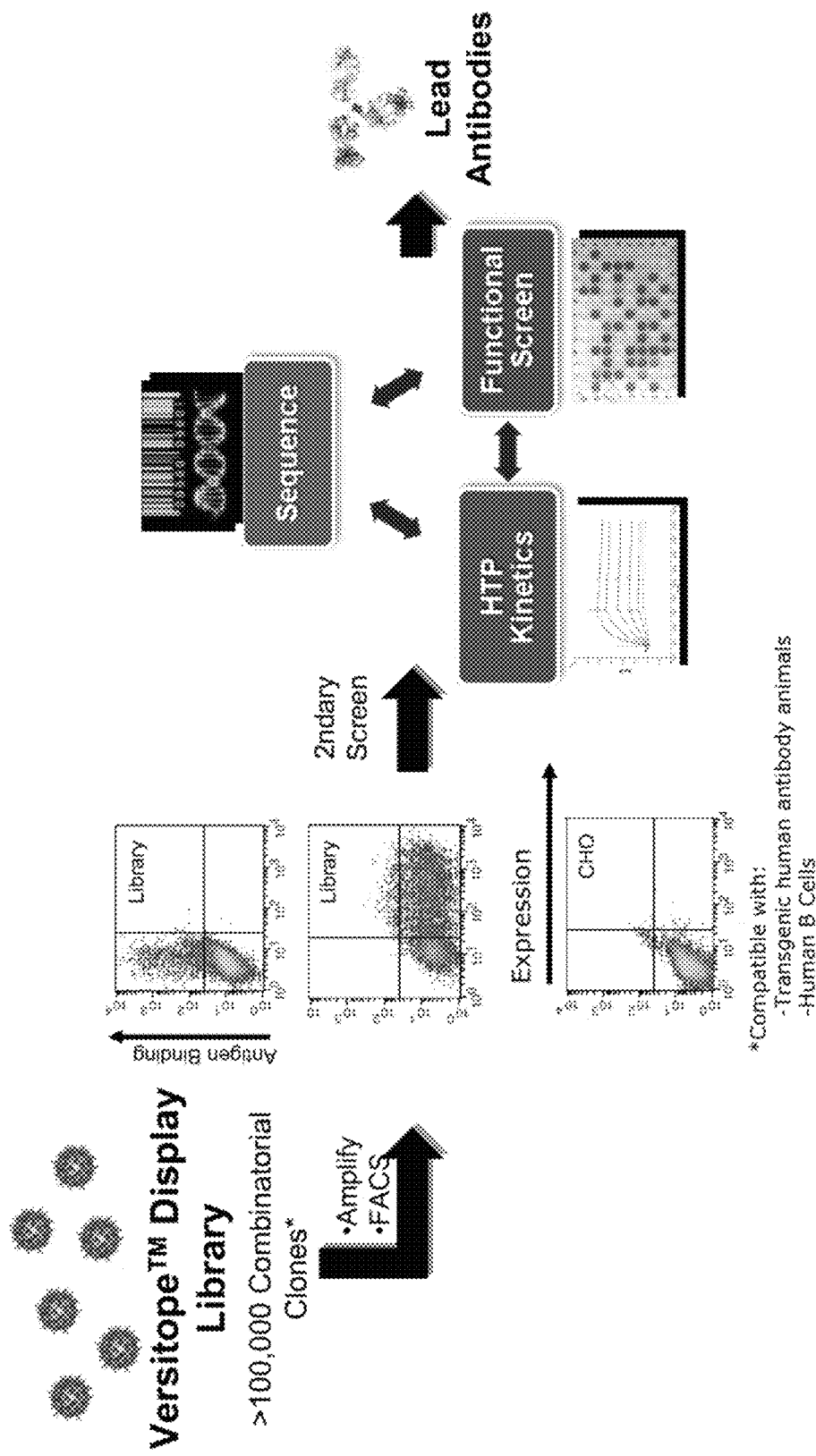
FIG. 3 shows a 100,000 member combinatorial library of clones that was grown (amplified) and screened via FACS for both antigen binding and expression. CHO cells without clones were also sorted as a negative control. A secondary screen can be performed. For example, sequencing, including high throughput, deep sequencing, kinetic assays or functional screens/assays can be performed to further identify or characterize lead antibodies.

In order to facilitate understanding of the examples provided herein, certain frequently occurring methods and/or terms will be described.

The term "affinity maturation" refers to the increase in average affinity of an immune response for an antigen. In nature, it can occur after repeated exposure to an antigen. A particularly preferred type of substitutional variant involves substituting one or more hypervariable region residues of a parent antibody (e.g. human antibody). Generally, the resulting variant(s) selected for further development will have improved biological properties relative to the parent antibody from which they are generated. A convenient way for generating such substitutional variants involves affinity maturation using techniques described herein or other techniques known to one of skill in the art, for example, phage display (Schier R., J. Mol. Biol., 263:551-67, 1996). The variants are then screened for their biological activity (e.g. binding affinity) as described herein, e.g. Biacore analysis. In order to identify hypervariable region residues which would be good candidates for modification, alanine scanning mutagenesis can be performed to identify hypervariable region residues contributing significantly to antigen binding. Antibodies with superior properties in one or more relevant assays can undergo further development.

The term "agent" is used herein to denote an antibody or antibody library. Agents are evaluated for potential activity as, for example, anti-neoplastics, anti-inflammatories or apoptosis modulators by inclusion in screening assays described hereinbelow. Agents are evaluated for potential activity as specific protein interaction inhibitors (i.e., an agent which selectively inhibits a binding interaction between two predetermined polypeptides but which does not substantially interfere with cell viability) by inclusion in screening assays described hereinbelow.

The term "amino acid" as used herein refers to any organic compound that contains an amino group (—NH$_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" means that the number of copies of a polynucleotide is increased.

The term "antibody", as used herein, refers to intact immunoglobulin molecules, as well as fragments of immunoglobulin molecules, such as Fab, Fab', (Fab')2, Fv, and SCA fragments, that are capable of binding to an epitope of an antigen.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

A single chain antibody ("SCA") is a genetically engineered single chain molecule containing the variable region of a light chain and the variable region of a heavy chain, linked by a suitable, flexible polypeptide linker.

The term "biobetter" refers to products which may carry the same therapeutic indication and work on the same or similar targets as those of previously approved novel biologic therapeutics. However, Biobetters are differentiated by unique characteristics which convey superior clinical efficacy. This may be through attributes such as reduced dose, extended half-life, convenient dosage formulation and increased safety. Since biobetters have mutations or other modifications, they are new compositions of matter, they require new clinical trials and are usually patent protected.

The term "biosimilar", also termed "follow-on biologic", refers to officially approved new versions of innovator biopharmaceutical products, following patent or exclusivity expiry.

The term "cell production host", or "manufacturing host", refers to a cell line used for the production or manufacturing of proteins. Eukaryotic cells such as mammalian cells, including, but not limited to human, mouse, hamster, rat, monkey cell lines as well as yeast, insect and plant cell lines. Prokaryotic cells can alternatively be utilized. In one aspect, a mammalian cell production host is selected from a member of the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells. In another aspect, the cell production host is a GS-NS0 or GS-CHOK1 cell line. In another aspect, the cell production host is selected from S. cerevisiae yeast cells; and picchia yeast cells. In another aspect, the cell production host is a bacterial cell line.

A molecule that has a "chimeric property" is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assembling a reassortment of partial molecular sequences. In a non-limiting aspect, a chimeric polynucleotide molecule may be prepared by synthesizing the chimeric polynucleotide using plurality of molecular templates, such that the resultant chimeric polynucleotide has properties of a plurality of templates.

The term "cognate" as used herein refers to a gene sequence that is evolutionarily and functionally related between species. For example, but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

The term "commercial scale" means production of a protein or antibody at a scale appropriate for resale.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482 by the homology alignment algorithm of Needlemen and Wuncsch J. Mol. Biol. 48: 443 (1970), by the search of similarity method of Pearson and Lipman Proc. Natl. Acad. Sci. (U.S.A.) 85: 2444 (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

As used herein, the term "complementarity-determining region" and "CDR" refer to the art-recognized term as exemplified by the Kabat and Chothia. CDR definitions are also generally known as supervariable regions or hypervariable loops (Chothia and Leks, 1987; Clothia et al., 1989; Kabat et al., 1987; and Tramontano et al., 1990). Variable region domains typically comprise the amino-terminal approximately 105-115 amino acids of a naturally-occurring immunoglobulin chain (e.g., amino acids 1-110), although variable domains somewhat shorter or longer are also suitable for forming single-chain antibodies. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. H means the variable heavy chain and L means the variable light chain. The CDR regions of an Ig-derived region may be determined as described in Kabat (1991). Sequences of Proteins of Immunological Interest, 5th edit., NIH Publication no. 91-3242 U.S. Department of Health and Human Services, Chothia (1987) J. Mol. Biol. 196, 901-917 and Chothia (1989) Nature, 342, 877-883.

The term "comprehensive" is used herein to refer to a technique of evolution wherein every possible change is made at each position of a template polynucleotide or template polypeptide and the polynucleotide or polypeptide is tested to confirm the intended change has been made by sequencing or some other technique. Comprehensive mutagenesis refers to mutating the DNA of a region of a gene encoding a protein that changes codon amino acid sequence of the protein and then determining via sequencing or other technologies that all mutations have been made and in the optimal case arrayed where every clone is in an identifiable position and/or uniquely tagged. Then screening of all the expressed mutants is performed to ensure that all are expressed comprehensively for an improved phenotype in order to provide guaranteed comprehensive coverage, i.e. CPE library with Comprehensive Screening comprising the BioAtla CPE process. Non-expressing clones in the screening system can also be simultaneously measured for expression to ensure that are not incorrectly labeled as negative or neutral mutations once enabled for expression an alternative system such as in vitro transcription and translation. Alternatively, sequencing could be performed on all clones after screening, but it should include all negative, neutral and up-mutant clones. Any mutants not identified are then be added in a second round of screening to yield and a true comprehensive mutagenesis and screening expression/activity system such as CPE.

The term "Comprehensive Positional Evolution" (CPE™) is used to describe an antibody evolution technology platform that can be used to enhance single or multiple antibody properties and binding characteristics. The CPE platform allows for the comprehensive mapping of the in vivo effects of every individual codon change within the protein for all sequence confirmed (or confirmed by other non-statistical confirmation method) 63 potential codon changes at each position within the protein. This comprehensive mutagenesis technology rapidly generates antibody variants by testing amino acid changes at every position along an antibody variable domain's sequence.

The term "Combinatorial Protein Synthesis" (CPS™) is used to describe combinatorial protein synthesis technologies that can be used to optimize the desired characteristics of antibodies by combining their best properties into a new, high-performance antibody. CPS™ can be used following CPE™ and can allow for the subsequent generation and in vivo selection of all permutations of improved individual codons for identification of the optimal combination or set of codon changes within a protein or antibody. The combination of these technologies can significantly expand the pool of antibody variants available to be screened and it significantly increases the probability of finding antibodies with single or multiple enhanced characteristics such as binding affinity, specificity, thermo-stability, expression level, effector function, glycosylation, and solubility.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "degrading effective" amount refers to the amount of which is required to process at least 50% of the substrate, as compared to substrate not contacted with the enzyme. Preferably, at least 80% of the substrate is degraded.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of (20)10 sequences, and (2) a pseudorandom 10-mer sequence of the 20 conventional amino acids can be any of (20)10 sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues), and the like, either segmentally or over the entire length of the individual selected library member sequence. Defined sequence kernels can refer to either amino acid sequences or polynucleotide sequences. Of illustration and not limitation, the sequences (NNK)10 and (NNM)10, wherein N represents A, T, G, or C; K represents G or T; and M represents A or C, are defined sequence kernels.

The term "deimmunization" as used herein relates to production of a variant of the template binding molecule, which is modified compared to an original wild type molecule by rendering said variant non-immunogenic or less immunogenic in humans. Deimmunized molecules according to the invention relate to antibodies or parts thereof (like frameworks and/or CDRs) of non-human origin. Corresponding examples are antibodies or fragments thereof as described in U.S. Pat. No. 4,361,549. The term "deimmunized" also relates to molecules, which show reduced propensity to generate T cell epitopes. In accordance with this invention, the term "reduced propensity to generate T cell epitopes" relates to the removal of T-cell epitopes leading to specific T-cell activation.

Furthermore, reduced propensity to generate T cell epitopes means substitution of amino acids contributing to the formation of T cell epitopes, i.e. substitution of amino acids, which are essential for formation of a T cell epitope. In other words, reduced propensity to generate T cell epitopes relates to reduced immunogenicity or reduced capacity to induce antigen independent T cell proliferation. In addition, reduced propensity to generate T cell epitopes relates to deimmunization, which means loss or reduction of potential T cell epitopes of amino acid sequences inducing antigen independent T cell proliferation.

The term "T cell epitope" as used herein relates to short peptide sequences which can be released during the degradation of peptides, polypeptide or proteins within cells and subsequently be presented by molecules of the major histocompatibility complex (MHC) in order to trigger the activation of T cells; see inter alia WO 02/066514. For peptides presented by MHC class II such activation of T cells can then induce an antibody response by direct stimulation of B cells to produce said antibodies.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like. Shuffling may be random or non-random.

As used in this invention, the term "epitope" refers to an antigenic determinant on an antigen, such as an IL-6 polypeptide, to which the paratope of an antibody, such as an anti-IL-6-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

The term "evolution" refers to a change in at least one property, characteristic or activity of a genetically or synthetically modified antibody when compared to a template antibody.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

The term "fragment" when applied to a nucleic acid sequence refers to a molecule that encodes for a portion, or a sub-portion, of an antibody molecule. For example, an HC CDR1 DNA fragment, may encode the entire heavy chain CDR1, or a truncated portion thereof.

In one aspect, certain methods provided herein provide for producing from a template polypeptide a set of progeny polypeptides in which a "full range of single amino acid substitutions" is represented at each amino acid position. As used herein, "full range of single amino acid substitutions" is in reference to the naturally encoded 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (introns) between individual coding segments (exons). "Genetic instability", as used herein, refers to the natural tendency of highly repetitive sequences to be lost through a process of reductive events generally involving sequence simplification through the loss of repeated sequences. Deletions tend to involve the loss of one copy of a repeat and everything between the repeats.

The term "heterologous" means that one single-stranded nucleic acid sequence is unable to hybridize to another single-stranded nucleic acid sequence or its complement. Thus, areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The term "humanized" is used to describe antibodies wherein complementarity determining regions (CDRs) from a mammalian animal, e.g., a mouse, are combined with a human framework region. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. In another aspect, besides mouse antibodies, other species can be humanized, such as, for example, other rodent, camel, rabbit, cat, dog, pig, horse, cow, fish, llama and shark. In a broad aspect, any species that produces antibodies can be utilized in the production of humanized antibodies. Additionally, the antibodies of the invention may be chimeric, human-like, humanized or fully human, in order to reduce their potential antigenicity, without reducing their affinity for their target. Chimeric, human-like and humanized antibodies have generally been described in the art. By incorporating as little foreign sequence as possible in the hybrid antibody, the antigenicity is reduced. Preparation of these hybrid antibodies may be carried out by methods well known in the art.

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," Kabat et al., 1987). The sequences of the framework regions of different light or heavy chains are relatively conserved within a species. As used herein, a "human framework region" is a framework region that is substantially identical (about 85 or more, usually 90-95 or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen. In accordance with this invention, a framework region relates to a region in the V domain (VH or VL domain) of immunoglobulins that provides a protein scaffold for the hypervariable complementarity determining regions (CDRs) that make contact with the antigen. In each V domain, there are four framework regions designated FR1, FR2, FR3 and FR4. Framework 1 encompasses the region from the N-terminus of the V domain until the beginning of CDR1, framework 2 relates to the region between CDR1 and CDR2, framework 3 encompasses the region between CDR2 and CDR3 and framework 4 means the region from the end of CDR3 until the C-terminus of the V domain; see, inter alia, Janeway, Immunobiology, Garland Publishing, 2001, 5th ed. Thus, the framework regions encompass all the regions outside the CDR regions in VH or VL domains. In one aspect of the disclosure, a single sequence is employed for framework 4 which is held constant through each member of the antibody library. In one aspect, the single sequence encoding framework region 4 is the most common sequence found in a human framework pool limited only to germline sequences from a functionally expressed antibodies.

The person skilled in the art is readily in a position to deduce from a given sequence the framework regions and, the CDRs; see Kabat (1991) Sequences of Proteins of Immunological Interest, 5th edit., NIH Publication no. 91-3242 U.S. Department of Health and Human Services, Chothia (1987) J. Mol. Biol. 196, 901-917 and Chothia (1989) Nature, 342, 877-883.

The benefits of this invention extend to "industrial applications" (or industrial processes), which term is used to include applications in commercial industry proper (or simply industry) as well as non-commercial industrial applications (e.g. biomedical research at a non-profit institution). Relevant applications include those in areas of diagnosis, medicine, agriculture, manufacturing, and academia.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The term "isolated" means that the material is removed from its original environment (e.g., the natural environment if it is naturally occurring). For example, a naturally-occurring polynucleotide or protein present in a living animal is not isolated, but the same polynucleotide or protein, separated from some or all of the coexisting materials in the natural system, is isolated. Such polynucleotides could be part of a vector and/or such polynucleotides or proteins could be part of a composition, and still be isolated in that such vector or composition is not part of its natural environment.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Maniatis et al., 1982, p. 146). Unless otherwise provided, ligation may be accomplished using known buffers and conditions with 10 units of T4 DNA ligase ("ligase") per 0.5 μg of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

The term "mammalian cell surface display" refers to a technique whereby a protein or antibody, or a portion of an antibody, is expressed and displayed on a mammalian host cell surface for screening purposes; for example, by screening for specific antigen binding by fluorescence-activated cell sorting. In one aspect, mammalian expression vectors are used for simultaneous expression of immunoglobulins as both a secreted and cell surface bound form as in DuBridge et al., US 2009/0136950, which is incorporated herein by reference. In another aspect, the techniques of Gao et al. are employed for a viral vector encoding for a library of antibodies or antibody fragments are displayed on the cell membranes when expressed in a cell as in Gao et al., US 2007/0111260, incorporated herein by reference. Whole IgG surface display on mammalian cells is known. For example, Akamatsuu et al. developed a mammalian cell surface display vector, suitable for directly isolating IgG molecules based on their antigen-binding affinity and biological activity. Using an Epstein-Barr virus-derived episomal vector, antibody libraries were displayed as whole IgG molecules on the cell surface and screened for specific antigen binding by a combination of magnetic beads and fluorescence-activated cell sorting. Plasmids encoding antibodies with desired binding characteristics were recovered from sorted cells and converted to the form for production of soluble IgG. Akamatsuu et al. J. Immunol. Methods 2007 327(1-2): 40-52; incorporated herein by reference. Ho et al. used human embryonic kidney 293T cells that are widely used for transient protein expression for cell surface display of single-chain Fv antibodies for affinity maturation. Cells expressing a rare mutant antibody with higher affinity were enriched 240-fold by a single-pass cell sorting from a large excess of cells expressing WT antibody with a slightly lower affinity. Furthermore, a highly enriched mutant was obtained with increased binding affinity for CD22 after a single selection of a combinatory library randomizing an intrinsic antibody hotspot. Ho et al. Isolation of anti-CD22 Fv with high affinity by Fv display on human cells, Proc Natl Acad Sci USA 2006 Jun. 20; 103(25): 9637-9642; incorporated herein by reference.

Beerli et al. used B cells specific for an antigen of interest which were directly isolated from peripheral blood mononuclear cells (PBMC) of human donors. Recombinant, antigen-specific single-chain Fv (scFv) libraries are generated from this pool of B cells and screened by mammalian cell surface display by using a Sindbis virus expression system. This method allows isolating antigen-specific antibodies by a single round of FACS. The variable regions (VRs) of the heavy chains (HCs) and light chains (LCs) were isolated from positive clones and recombinant fully human antibodies produced as whole IgG or Fab fragments. In this manner, several hypermutated high-affinity antibodies binding the Qβ virus like particle (VLP), a model viral antigen, as well as antibodies specific for nicotine were isolated. All antibodies showed high expression levels in cell culture. The human nicotine-specific mAbs were validated preclinically in a mouse model. Beerli et al., Isolation of human monoclonal antibodies by mammalian cell display, Proc Natl Acad Sci USA. 2008 Sep. 23; 105(38): 14336-14341; incorporated herein by reference.

Yeast cell surface display is also known, for example, see Kondo and Ueda 2004, Yeast cell-surface display-applications of molecular display, Appl. Microbiol. Biotechnol., 64(1): 28-40, which describes for example, a cell-surface engineering system using the yeast *Saccharomyces cerevisiae*. Several representative display systems for the expression in yeast *S. cerevisiae* are described in Lee et al, 2003, Microbial cell-surface display, TRENDS in Bitechnol. 21(1): 45-52. Also Boder and Wittrup 1997, Yeast surface display for screening combinatorial polypeptide libraries, Nature Biotechnol., 15(6): 553.

The term "manufacturing" refers to production of a protein at a sufficient quantity to permit at least Phase I clinical testing of a therapeutic protein, or sufficient quantity for regulatory approval of a diagnostic protein.

The term "missense mutation" refers to a point mutation where a single nucleotide is changed, resulting in a codon that codes for a different amino acid. Mutations that change an amino acid to a stop codon are called nonsense mutations.

As used herein, a "molecular property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting—examples of molecular properties to be evolved include enzymatic activities at specified conditions, such as related to temperature; salinity; pressure; pH; and concentration of glycerol, DMSO, detergent, and/or any other molecular species with which contact is made in a reaction environment. Additional particularly relevant—but by no means limiting examples of molecular properties to be evolved include stabilities—e.g., the amount of a residual molecular property that is present after a specified exposure time to a specified environment, such as may be encountered during storage.

The term "Multidimensional Epitope Mapping" (MEM) refers to the identification of the epitope and the resolution of the amino acids that are important for antibody binding. Information about the binding sites (epitopes) of proteins recognized by antibodies is important for their use as biological or diagnostic tools as well as for understanding their mechanisms of action. However, antigens are highly diverse, in their primary sequence as well as in three dimensional structures. Epitopes generally fall into 3 categories: 1) linear epitopes, i.e. the antibody binds to residues on a linear part of the polypeptide chain, 2) conformational epitopes, where the binding site is formed by a structural element (e.g. α-helix, loop), 3) discontinuous epitopes where two or more separate stretches of the polypeptide chain which are brought together in the three dimensional structure of the antigen form the binding surface.

The term "mutating" refers to creating a mutation in a nucleic acid sequence; in the event where the mutation occurs within the coding region of a protein, it will lead to a codon change which may or may not lead to an amino acid change.

The term "mutations" means changes in the sequence of a wild-type nucleic acid sequence or changes in the sequence of a peptide or polypeptides. Such mutations may be point mutations such as transitions or transversions. The mutations may be deletions, insertions or duplications.

As used herein, the degenerate "N,N,G/T" nucleotide sequence represents 32 possible triplets, where "N" can be A, C, G or T.

As used herein, the degenerate "N,N,N" nucleotide sequence represents 64 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular protein—as well as other synonymous terms—refer to a DNA sequence which is transcribed and translated into a protein when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promoter sequence will be found a transcription initiation site (conveniently defined by mapping with nuclease S1) as well as protein binding domains (consensus sequences) responsible for the binding of RNA polymerase.

The terms "nucleic acid encoding an protein" or "DNA encoding an protein" or "polynucleotide encoding an protein" and other synonymous terms encompasses a polynucleotide which includes only coding sequence for the protein as well as a polynucleotide which includes additional coding and/or non-Cq3 coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present invention provides a "nucleic acid construct" or alternatively a "nucleotide construct" or alternatively a "DNA construct". The term "construct" is used herein to describe a molecule, such as a polynucleotide (e.g., a phytase polynucleotide) may optionally be chemically bonded to one or more additional molecular moieties, such as a vector, or parts of a vector. In a specific—but by no means limiting—aspect, a nucleotide construct is exemplified by a DNA expression DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation (e.g., Mg++, Ca++); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants.

The term "population" as used herein means a collection of components such as polynucleotides, portions or polynucleotides or proteins. A "mixed population: means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g., glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When two or more chemical modification (e.g. two proteolytic cleavages, or a proteolytic cleavage and a deglycosylation) can be distinguished en route to the production of a mature molecule, the reference precursor molecule may be termed a "pre-pro-form" molecule.

A "property" can describe any characteristic, including a physical, chemical, or activity characteristic property of a protein or antibody to be optimized. For example, in certain aspects, the predetermined property, characteristic or activity to be optimized can be selected from is selected from reduction of protein-protein aggregation, enhancement of protein stability, increased protein solubility, increased protein pH stability, increased protein temperature stability, increased protein solvent stability, increased selectivity, decreased selectivity, introduction of glycosylation sites, introduction of conjugation sites, reduction of immunogenicity, enhancement of protein expression, increase in antigen affinity, decrease in antigen affinity, change in binding affinity, change in immunogenicity, change in catalytic activity, pH optimization, or enhancement of specificity. Other properties or characteristics to be optimized include antibody stability in vivo (e.g., serum half-lives) and/or in vitro (e.g., shelf-life); melting temperature (Tm) of the antibody (e.g., as determined by differential scanning calorimetry (DSC) or other method known in the art), the pI of the antibody (e.g., as determined Isoelectric focusing (IEF) or other methods known in the art); solubility; binding properties (e.g., antibody-antigen binding constants such as, Ka, Kd, $K_{on}$, $K_{off}$), equilibrium dissociation constant ($K_D$); antibody solubility (e.g., solubility in a pharmaceutically acceptable carrier, diluent or excipient), effector function (e.g., antibody dependent cell-mediated cytotoxicity (ADCC)); expression level and production levels (e.g., the yield of an antibody from a cell).

An "optimized" property refers to a desirable change in a particular property in a mutant protein or antibody compared to a template antibody. In one aspect, an optimized property refers to wherein the improvement is between about 1% and 500%, relative to the template antibody or is between about 2 fold and 1000 fold, relative to the template antibody.

As used herein, the term "pseudorandom" refers to a set of sequences that have limited variability, such that, for example, the degree of residue variability at another position, but any pseudorandom position is allowed some degree of residue variation, however circumscribed.

"Quasi-repeated units", as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reasserted by this approach, they can be referred to as "quasi-repeated" units.

As used herein "random peptide library" refers to a set of polynucleotide sequences that encodes a set of random peptides, and to the set of random peptides encoded by those polynucleotide sequences, as well as the fusion proteins contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or noncovalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

"Recombinant" proteins refer to enzymes produced by recombinant DNA techniques, i.e., produced from cells transformed by an exogenous DNA construct encoding the desired protein. "Synthetic" proteins are those prepared by chemical synthesis.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

"Repetitive Index (RI)", as used herein, is the average number of copies of the quasi-repeated units contained in the cloning vector.

The term "saturation" refers to a technique of evolution wherein every possible change is made at each position of a template polynucleotide or template polypeptide; however the change at each position is not confirmed by testing, but merely assumed statistically wherein the majority of possible changes or nearly every possible change is estimated to occur at each position of a template. Saturation mutagenesis refers to mutating the DNA of a region of a gene encoding a protein that changes codon amino acid sequence of the protein and then screening the expressed mutants of essentially all of the mutants for an improved phenotype based on statistical over-sampling that approaches comprehensive coverage, but does not guarantee complete coverage.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25-50 nucleotides, wherein the percentage of sequence identity is calculated by comparing the reference sequence to the polynucleotide sequence which may include deletions or additions which total 20 percent or less of the reference sequence over the window of comparison.

The term "silent mutation" refers to a codon change that does not result in an amino acid change in an expressed polypeptide and is based on redundancy of codon usage for amino acid insertion.

As known in the art "similarity" between two proteins is determined by comparing the amino acid sequence and its conserved amino acid substitutes of one protein to the sequence of a second protein. Similarity may be determined by procedures which are well-known in the art, for example, a BLAST program (Basic Local Alignment Search Tool at the National Center for Biological Information).

As used herein, the term "single-chain antibody" refers to a polypeptide comprising a VH domain and a VL domain in polypeptide linkage, generally liked via a spacer peptide (e.g., [Gly-Gly-Gly-Gly-Ser]$_x$), and which may comprise additional amino acid sequences at the amino- and/or carboxy-termini. For example, a single-chain antibody may comprise a tether segment for linking to the encoding polynucleotide. As an example a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361-368, which is incorporated herein by reference), most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

"Stringent hybridization conditions" means hybridization will occur only if there is at least 90% identity, preferably at least 95% identity and most preferably at least 97% identity between the sequences. See Sambrook et al., 1989, which is hereby incorporated by reference in its entirety.

Also included in the invention are polypeptides having sequences that are "substantially identical" to the sequence of a polypeptide, such as one of any SEQ ID NO disclosed herein. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site the molecule, and provided that the polypeptide essentially retains its behavioral properties. For example, one or more amino acids can be deleted from a phytase polypeptide, resulting in modification of the structure of the polypeptide, without significantly altering its biological activity. For example, amino- or carboxyl-terminal amino acids that are not required for phytase biological activity can be removed. Such modifications can result in the development of smaller active phytase polypeptides.

The present invention provides a "substantially pure protein". The term "substantially pure protein" is used herein to describe a molecule, such as a polypeptide (e.g., a phytase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

DETAILED DESCRIPTION OF THE INVENTION

The present invention relates to methods that are useful for producing high affinity monoclonal antibodies comprising screening and isolating B cells that recognize a target antigen. More particularly, the present invention further relates to methods that are useful in producing at least one recombinant monoclonal antibody from B cells that is specific for a target antigen. (The present invention does not rely on or utilize immortalized cells such as hybridoma cells). The methods described herein for generation of high diversity, high affinity antibodies are termed Versitope™ Antibody Generation. In a preferred embodiment, full length, surface displayed antibodies, are produced. Surface display systems can be yeast, mammalian, or bacterial. Surface display gives rise to a "super avidity" effect which can be beneficial for certain selection processes. For example, cell surface display technology is beneficial for selecting weak epitopes; thus, in the present invention, epitope coverage is maximized in comparison to methods which only screen for stronger binding epitopes.

For example, B cells expressing a desired immunoglobulin may be screened and selected, and the sequence(s) of the immunoglobulin's heavy (e.g., $V_H$ region) and/or light (e.g., $V_L$ region) chains can be identified, cloned and characterized. The methods disclosed herein significantly improve the efficiency of monoclonal antibody production, while maintaining high affinity and epitope coverage for target antigens. It will be appreciated that in many cases, more than one recombinant monoclonal antibody with suitable specificity will be obtained using the methods of the present invention; thus reference to "recombinant antibodies" herein refers to one or more recombinant antibodies. The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions).

The invention takes advantage of the expression of membrane-associated immunoglobulins on B cells to identify and select specific B cells in splenocytes or other biological samples (e.g., blood). B cells that express a desired immunoglobulin are detected and selected, for example, by fluorescent or luminescent markers using fluorescence activated cell sorting (FACS) or panning Colorimetric, radioactive or other methods and assays may be used, as well.

In another aspect of the present invention, all B-cells are isolated from non-immunized non-human or human hosts, and B-cell genes are isolated by, for example, amplification using PCR or other strategies, as described herein.

Thus, in a preferred aspect, the present invention provides methods of producing recombinant antibodies which comprise the step of screening, via fluorescence activated cell sorting (FACS), panning or another screening method, B cells from a non-human host immunized with a target antigen, or a human immunized host, to generate a B cell library enriched in B cells capable of binding to the target antigen. Alternatively, B cells are isolated from human or non-human non-immunized hosts, recombinant antibodies are produced. Such methods are shown schematically in FIG. 1 and are explained in detail herein.

The term immunoglobulin or antibody, as used herein, refers to intact immunoglobulin molecules, as well as derivatives or fragments of immunoglobulin molecules, such as Fab, Fab', (Fab')2, Fv, and single chain antibody fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows.

A Fab fragment consists of a monovalent antigen-binding fragment of an antibody molecule, and can be produced by digestion of a whole antibody molecule with the enzyme papain, to yield a fragment consisting of an intact light chain and a portion of a heavy chain. Derivatives include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

As used herein, a ligand is a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

A Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

As used herein, the term "single-chain antibody" ("SCA") refers to a polypeptide comprising a $V_H$ domain and a $V_L$ domain in polypeptide linkage, generally liked via a spacer peptide (e.g., [Gly-Gly-Gly-Gly-Ser]$_x$), and which may comprise additional amino acid sequences at the amino- and/or carboxy-termini. For example, a single-chain antibody may comprise a tether segment for linking to the encoding polynucleotide. As an example a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361-368, which is incorporated herein by reference), most frequently encoded by a rodent, non-human primate, avian, porcine, bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

As noted above, the present invention relates to methods that are useful in producing recombinant monoclonal antibodies. Specifically, methods that are useful in producing recombinant monoclonal antibodies derived from B cell libraries that bind to the target antigen obtained via FACS, panning or other methods of screening are contemplated.

Although reference is made to binding to a target antigen, it should be understood that multiple antigens can be screened to select for multifunctional antibodies. Multiple antigens includes two or more different antigens or two or more different epitopes on the same target.

In a first embodiment of the invention, (the "natural diversity" approach), the original variable heavy and variable light chain pairing from the host is maintained; that is the antibodies generated are "naturally paired". This is sometimes desirable as clearly it is likely that the very presence of a particular original pairing of light and heavy chains in vivo in the B cells derived from the immunochallenged host means that this particular combination of heavy and light chains is likely to be functional in recognizing antigen.

In this embodiment, the invention provides a method of producing a target antigen-specific recombinant monoclonal antibody comprising screening, via fluorescence activated cell sorting (FACS) or other method, a population of B cells from a non-human or human host immunized with a target antigen to generate a B cell library enriched in B cells capable of binding to the target antigen; amplifying cDNA obtained from mRNA expressed in a single B cell to prepare an immunoglobulin library comprising $V_H$ and $V_L$ domains (single cell amplification is performed for a plurality of B cells in the B cell library); cloning the immunoglobulin library into an expression vector to form a library of expression vectors capable of expressing the $V_H$ and $V_L$ domains, such that the $V_H$ and $V_L$ domains are naturally paired; using the library of expression vectors to express the $V_H$ and $V_L$ domains in an expression system to form an antibody library, wherein the antibodies comprise naturally paired $V_H$ and $V_L$ domains; screening the antibody library for binding to the target antigen; and characterizing the antibodies capable of binding to the target antigen. In this manner, one or more target antigen-specific recombinant antibodies are produced.

In another embodiment, the naturally paired antibodies are derived from a non-immunochallenged host.

The present invention also includes another embodiment in which additional light chain and heavy chain combinations are created (the "high diversity approach"). In this embodiment, the invention provides a method of producing a target-antigen specific recombinant monoclonal antibody comprising screening, via fluorescence activated cell sorting (FACS), panning or other screening method, B cells from a non-human or human host immunized with a target antigen to generate a B cell library enriched in B cells capable of binding to the target antigen; amplifying cDNA obtained from mRNA expressed in the B cell library to prepare an immunoglobulin library comprising $V_H$ and $V_L$ domains; generating antibodies or fragments or derivatives from the $V_H$ and $V_L$ domains using a biological display system to obtain a cell population displaying the antibodies or fragments or derivatives, whereby the antibodies or fragments or derivatives comprise light chain/heavy chain combinations that were not present in the B cells in vivo, that is, the number of combinations generated is more than the number of B cells in the enriched B cell library; screening, via FACS, the cell population with the target antigen to identify a subset of cells displaying antibodies capable of binding to the target antigen; and characterizing the antibodies capable of binding to the target antigen. In this manner, one or more target antigen-specific recombinant antibodies may be produced.

In another embodiment, the antibodies are derived from a non-immunochallenged host.

In alternate embodiments, the invention provides methods of generating and identifying a recombinant antibody that binds at least one target antigen comprising screening B cells to generate a B cell library enriched in B cells capable of binding to the at least one target antigen; amplifying cDNA obtained from mRNA expressed in the B cell library to prepare an immunoglobulin library comprising $V_H$ domains; generating antibodies from the $V_H$ domains and at least one $V_L$ domain from another source, whereby the antibodies comprise light chain/heavy chain combinations; and screening the antibodies with the at least one target antigen to identify a subset of antibodies capable of binding to the at least one target antigen.

These approaches are described in detail below.

Preparation of the B Cell Library

In the present invention, recombinant antibodies are derived from B cells. In one embodiment, immunization of a suitable non-human host, i.e., a non-human animal, and preparation and isolation of B cells may be carried out according to standard techniques. A suitable animal (e.g., rabbit, a mouse, a rat, a hamster, a guinea pig, a camel or a goat) may be immunized with an antigen of interest, or an immunogenic portion thereof. Methods for immunizing non-human animals such as mice, rats, sheep, goats, pigs, cattle and horses are well known in the art. See, e.g., Harlow and Lane, Antibodies: A Laboratory Manual, New York: Cold Spring Harbor Press, 1990. In another aspect of the present invention, blood from previously exposed or immune challenged patient(s) is used, and B cells are isolated therefrom. In yet another aspect, isolated B cells from more than one species are pooled.

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which can be used to generate a B cell library. Transgenic human antibody animals prepared by other methods known to the skilled artisan can also be used as sources of B cells in the present invention. For example, the "minilocus" approach that is typified by GenPharm International, Inc. and the Medical Research Council. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described or related to work in U.S. Pat. No. 5,545,807 to Surani et al., for example.

The antigen or epitope(s) thereof in accordance with the present invention may be small peptides, proteins, or non-peptide immunogenic compounds. The antigen or immunogen may be a full length protein of interest or an immunogenic peptide derived from the antigen. In some embodiments the immunogen is a peptide of from 7 to 20 amino acids in length, preferably about 8 to 17 amino acids in length. Peptide antigens suitable for producing antibodies of the invention may be designed, constructed and employed in accordance with well-known techniques. See, e.g., Harlow & Lane Eds., Cold Spring Harbor Laboratory (1988); Czernik, Methods In Enzymology, 201: 264-283 (1991); Merrifield, J. Am. Chem. Soc. 85: 21-49 (1962)).

Immunogenic compositions often vary in immunogenicity. The amount of immunogen composition used in the production of antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given.

It is often necessary to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Recognized means for conjugating a polypeptide to a carrier protein are well known and include glutaraldehyde, m-maleimidobenzoyl-N-hydroxysuccinimide ester, carbodiimides and bis-diazotized benzidine.

The immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants, RIBI (muramyl dipeptides), ISCOM (immunostimulating complexes), and aluminum hydroxide adjuvant.

An enhancement of antibody producing cells will occur as part of the natural immune response to target antigen, as antibody producing cells (B cells/B lymphocytes) which are capable of making antibodies directed to the target antigen in question will be stimulated to proliferate and will therefore increase in number. Such an enhancement will occur over time and reach a maximum, then will naturally tail off once the amount of antigen in question is reduced or eliminated as there will be no further antigen-induced stimulation of B cell proliferation and the existing B cells will be removed by naturally occurring biological mechanisms, e.g. by cell death.

Put another way, the hosts from which the recombinant antibodies of the present invention are derived have been immunochallenged/exposed to the target antigen(s) at a time point such that they are still in an active phase of immune response to the target antigen, etc., in question. Hosts in an active phase of immune response can readily be identified by a person skilled in the art. For example, such hosts will be actively producing specific antibodies in response to target antigen. Thus, for example, the presence of a high serum titer of specific antibodies to the target antigen in question is indicative of such appropriate hosts. Preferably this high serum titer of specific antibodies will be combined with a relatively low serum titer of non-specific antibodies, thereby evidencing the enhancement of the antibody producing cells. Again the serum titers of candidate hosts can be compared to the serum titers of naive donors or healthy donors as described above in order to assess whether or not the serum titer of antibodies to a particular target antigen is significantly higher in the candidate hosts.

Thus, there is a time window after exposure to antigen in which the B cells from the host which are used to provide the genetic material for the antibody expression libraries of the invention can optimally be isolated in order to obtain the benefits of the enhanced B-cell population. The length of time after exposure to antigen to meet this requirement may vary from host to host, may depend on the foreign agent or target antigen in question, the source of the B cells in the host (e.g., circulating B cells as opposed to e.g., B cells in the lymphoid tissues) and also on whether or not a primary, secondary or further response to the target antigen is being mounted. However, any time period can be used, since the methods of the present invention are less sensitive than hybridoma technologies.

The suitability of a host can readily be determined if desired, by taking a sample of antibody producing cells (B-cells) from the host, e.g., by taking a blood sample, and carrying out a standard in vitro assay (e.g., an ELISA assay or ELISPOT assay, Czerkinsky et al., 1983, J. Immunol. Methods, vol 65:109-121) using the relevant target antigen as a target antigen and measuring the degree of immunoreaction. Preferably the degree of immunoreaction with a control antigen is also assessed in order to provide an indication of the level of enhancement of the sample for the desired antibodies. A low or relatively low degree of immunoreaction with a control antigen is evidence that the expression libraries derived from these hosts will contain fewer irrelevant antibodies, i.e. will be enriched and diverse for antibodies against the antigen in question. The selection of an appropriate host as a source of antibody producing cells from which to derive antibodies may also depend on the type of antibodies it is desired to have in the repertoire. For example, if it is desired to generate a library comprising an enriched IgM repertoire, then the B cells will preferably be isolated after a first exposure of a host to the target antigen, agent, disease, etc. On the other hand, if it is desired that the repertoire reflects an enriched pool of antibodies in the IgG format, which is the preferred format, or another format such as IgA, IgD or IgE, the B cells may be isolated after a first exposure to the target antigen, etc., but more preferably are isolated after a second or subsequent exposure.

This immunoreaction measurement can be done one or more times to monitor the progress and degree of a host's immune response to an antigen and assess (by, for example, an appropriate comparison with a naive donor) whether or not a suitably enhanced population of B cells is present. In this way the optimum time to harvest antibody producing cells (which contain the genetic material from which the expression library will be derived) from a host can be identified. In addition, hosts which are not appropriate or are no longer appropriate to provide material for library generation can readily be identified.

In one aspect, the method comprises the use of the ELISPOT assay, mentioned above (or other suitable assay). Such an assay is especially suitable for testing circulating B cells and is based on the coating of a surface with the particular target antigen to which it is desired to obtain antibodies (and by which the host is being immunochallenged) and adding a defined number of B cells. B cells secreting antibodies that bind to the antigen can be detected by conventional ELISA detection. This assay only detects B cells which are secreting specific antibodies and not B cells with specific membrane bound antibodies, so the actual number of B cells with specific antibodies may actually be higher than the test suggests.

In enzyme-linked immunosorbent assay (ELISA), a sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample.

Traditional ELISA typically involves chromogenic reporters and substrates which produce some kind of observable color change to indicate the presence of antigen or analyte. Newer ELISA-like techniques utilize fluorogenic, electrochemiluminescent, and real-time PCR reporters to create quantifiable signals. These new reporters can have various advantages including higher sensitivities and multiplexing. Technically, newer assays of this type are not strictly ELISAs as they are not "enzyme-linked" but are instead linked to some non-enzymatic reporter. However, given that the general principles in these assays are largely similar, they are often grouped in the same category as ELISAs.

The process of boosting and titering is repeated until a suitable titer is achieved. When a desired level of immunogenicity is obtained, antibody-producing B cells are isolated from the animal. The antibody-producing B cells may be isolated from the spleen, lymph nodes or peripheral blood, cells from bone marrow, tonsils or any other secondary lymphoid tissue, tumor infiltrating lymphocytes, tissues or organs affected by an autoimmune disease, or from any other tissues or fluids or other samples known to harbor antibody producing B cells. In some cases, the appropriate sources of B cells will depend on the disease or immunochallenge to which antibodies are sought. The main requirement for the non-human hosts from which the antibodies of the present embodiment of the present invention are derived is that they have been immunochallenged/exposed to the target antigen (s) at a time point such that they still contain a repertoire of antibody producing cells which are enriched with cells producing antibodies directed to the target antigen or antigens. Individual B cells may be isolated and screened (as described below) to identify cells producing an immunoglobulin specific for the antigen of interest. Identified cells may then used in various embodiments of the invention.

In certain embodiments, antibody-producing B cells can be isolated from the blood or other biological samples of an animal or human suffering from an infection, cancer, an autoimmune condition, or any other diseases to identify a pathogen-, tumor-, and disease-specific antibody of potential clinical significance. For example, the animal may be one that was exposed to and/or who can make useful antibodies against an infectious agent (e.g., viruses, bacteria, parasites, prions, etc). Certain B cells from immunized hosts make antibodies to the target antigen or antigens in question. In the present invention the lymphocyte pool is enriched for the desired B cells by screening and sorting the cells using fluorescence-activated cell sorting (FACS), magnetic activated cell sorting (MACS), panning or other screening method to generate a B cell library before antibodies or an expression library is/are made. In contrast to prior art enrichment methods, which provide only a few subsets of B cells expressing different antibodies, and therefore only a few naturally occurring combinations of variable heavy ($V_H$) and variable light ($V_L$) genes, the B cell library of the present invention contains at least 10 subsets of B cells expressing different antibodies, and in some embodiments at least 1000 subsets of B cells expressing different antibodies with an affinity to the target antigen, and in still further embodiments, at least $10^3$, $10^4$, $10^5$, $10^6$, $10^7$, or $10^8$ subsets of B cells expressing different antibodies. The methods of the present invention maximize B cell recovery, and afford very high diversity.

In other embodiments, B cells are from non-immunized human or non-human donors are utilized. The naive repertoire of an animal (the repertoire before antigen challenge) provides it with antibodies that can bind with moderate affinity ($K_a$ of about $10^6$ to $10^7$ $M^{-1}$) to essentially any non-self molecule. The sequence diversity of antibody binding sites is not encoded directly in the germline but is assembled in a combinatorial manner from V gene segments Immunizations trigger any B cell making a $V_H$-$V_L$ combination that binds the immunogen to proliferate (clonal expansion) and to secrete the corresponding antibody as noted above. However, the use of spleen cells and/or B cells or other peripheral blood lymphocytes" PBLs from an unimmunized donor provides a better representation of the possible antibody repertoire, and also permits the construction of a B-cell subsequent antibody library using any animal (human or non-human) species.

Generation of a B cell library can be accomplished via FACS sorting or panning, as stated above. FACS is a powerful system which not only quantifies the fluorescent signal but also separates the cells that contain preselected characteristics (such as fluorescence intensity, size and viability) from a mixed population. Laser light is directed at individual cells as they flow through the FACS. A light scatter pattern is generated when the dense nuclear material of the cell interferes with the path of the laser beam. Thus, cells can be selected at random based on their ability to scatter laser light. In one embodiment, the antigen of interest (or an antigenic portion thereof) is attached directly or indirectly to a fluorescent marker, such as fluoroscein isothiocyanate (FITC) or any of a number of fluorescent dye molecules well known in the art, and detected by the FACS sorter. The FACS sorter is a cytofluorimetric device that allows the analysis and isolation of cell populations according to the scattering and the fluorescent signals of those cells. Therefore, the cells get labeled with fluorescent dyes which are usually coupled to antibodies that recognize a certain cell type. The resulting signals are detected using e.g. a photo multiplier, CCD- and CMOS-detectors, and photon counting assemblies (see, e.g., Baumgarth and Roederer, J Immunol Methods (2000) 243:77-97).

Panning refers to the use of surfaces coated with target antigen to separate or concentrate specific cells with appropriate receptors (in this case, antibodies). For example, one method of enriching for antigen-reactive B cells is panning on a plastic dish that has been coated with antigen. Antigen reactive B cells may then be eluted from the plastic dish and used for isolation of nucleic acid. Both FACS analysis and panning (as well as other separation methods), may also be performed in a manner so as to enrich for B cells as opposed to antigen-reactive B cells. The advantage of selecting for total B cells populations is that one is more likely to include plasma cells, or B cells actively secreting immunoglobulin, that might be missed in procedures that require the presence of cell-surface immunoglobulin for detection.

The conventional MACS procedure is described by Miltenyi et al., "High Gradient Magnetic Cell Separation with MACS," Cytometry 11:231-238 (1990). To sort cells by MACS, one labels cells with magnetic beads and passes the cells through a paramagnetic separation column. The separation column is placed in a strong permanent magnet, thereby creating a magnetic field within the column. Cells that are magnetically labeled are trapped in the column; cells that are not pass through. One then elutes the trapped cells from the column.

Recombinant Methods for Constructing Nucleic Acids
Amplification of B Cell Genetic Material The present invention utilizes steps in which nucleic acids are manipulated in order to produce recombinant monoclonal antibodies. In a general sense, in each embodiment of the invention, amplification of B cell genetic material, e.g. reverse transcription polymerase chain reaction (RT-PCR) is employed to generate cDNA. In the natural diversity approach, amplification of B cell genetic material RT-PCR is performed on single cells in the B cell library, while in the high diversity approach, RT-PCR is performed on the pooled B cell library. For full length antibody molecules, the immunoglobulin genes can be obtained from genomic DNA or mRNA of B cells. Antibody heavy and light chains are cloned in a mammalian vector system. Assembly is documented with double strand sequence analysis. The antibody construct can be expressed in other human or mammalian host cell lines. The construct can then be validated by transient transfection assays and Western blot analysis of the expressed antibody of interest. Stable cell lines with the highest productivity can be isolated and screened using rapid assay methods.

The nucleic acid compositions of this invention, such as RNA, cDNA, genomic DNA, or any combination thereof, can be derived from biological sources, i.e., B cells, using any number of recombinant, synthetic, and/or purification methodologies known to those of skill in the art. By "nucleic acid" or "recombinant nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al.; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al.; U.S. Pat. No. 4,889,818 to Gelfand, et al.; U.S. Pat. No. 4,994,370 to Silver, et al.; U.S. Pat. No. 4,766,067 to Biswas; U.S. Pat. No. 4,656,134 to Ringold) and RNA mediated amplification that uses antisense RNA to the target sequence as a template for double-stranded DNA synthesis (U.S. Pat. No. 5,130,238 to Malek, et al., with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

In some embodiments, oligonucleotide probes that selectively hybridize, under stringent conditions, to the polynucleotides of the present invention are used to identify the desired sequence in a cDNA (or genomic) DNA library. An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification. The isolation of RNA, and construction of cDNA and genomic libraries, is well known to those of ordinary skill in the art. (See, e.g., Sambrook, et al. Molecular Cloning: A Laboratory Manual, 2nd Edition, Cold Spring Harbor Press, Cold Spring Harbor, N.Y. (1989) and Ausubel et al., eds. Current Protocols in Molecular Biology (1987-1993)). "Stringent hybridization conditions" means hybridization will occur only if there is at least 90% identity, preferably at least 95% identity and most preferably at least 97% identity between the sequences. See Sambrook et al., 1989, which is hereby incorporated by reference in its entirety.

Conveniently, the method steps described herein, such as amplification, screening, and the like, may be carried out in a multiplex assay format employing a solid phase on which a plurality of substrates, e.g., antigens, and the like, are immobilized, such as an array. In some embodiments, the array is a protein biochip. Using protein biochips, hundreds and even thousands of antigens can be screened. As used herein, "array," "microarray," or "biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface, and therefore, function as probes. A "protein biochip" refers to a biochip adapted for the capture of polypeptides. Many protein biochips are described in the art. Methods of producing polypeptide arrays are described, e.g., in De Wildt et al., 2000, Nat. Biotechnol. 18:989-994; Lueking et al., 1999, Anal. Biochem. 270:103-111; Ge, 2000, Nucleic Acids Res. 28, e3, 1-VII; MacBeath and Schreiber, 2000, Science 289: 1760-1763; WO 01/40803 and WO 99/51773A1. Use of arrays allows a number of the steps, such as screening, to be performed robotically and/or in a high-throughput manner Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

Upon capture on a biochip, analytes can be detected by a variety of detection methods selected from, for example, a gas phase ion spectrometry method, an optical method, an electrochemical method, atomic force microscopy and a radio frequency method. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods Immunoassays in various formats (e.g., ELISA) are popular methods for detection of analytes captured on a solid phase. Electrochemical methods include voltametry and amperometry methods. Radio frequency methods include multipolar resonance spectroscopy.

In some embodiments of the invention, e.g., the natural diversity approach for preparing monoclonal antibodies, techniques which have been established for working with single cells are employed. One technique incorporates a special accessory which can be used in FACS to deflect single cells into separate containers. Such accessories are commercially available and well-known in the art. Such accessories are useful for dispensing single cells into selected compartments of, for example, standard 96 well microtiter culture plates. Alternatively, cells may be deposited into a microtiter plate at a limiting dilution to ensure single cell deposition.

A second technique is PCR performed on single B cells to amplify the $V_H$ and $V_L$ segments. In the natural diversity approach, single cell PCR is used to retain the native pairing of $V_L$ and $V_H$ in the single cell. The specificity of an antibody is determined by the complementarity determining regions (CDRs) within the light chain variable regions ($V_L$) and heavy chain variable regions ($V_H$).

Methods for performing single-cell PCR are well known in the art (e.g., Larrick, J. W. et al., Bio/Technology 7:934 (1989)). For example, antibody-producing B-cells from the B cell library may be fixed with a fixative solution or a solution containing a chemical such as formaldehyde, glutaraldehyde or the like. The cells are then permeabilized with a permeabilization solution comprising for example a detergent. The fixing and permeabilization process should provide sufficient porosity to allow entrance of enzymes, nucleotides and other reagents into the cells without undue destruction of cellular compartments or nucleic acids therein. Addition of enzymes and nucleotides may then enter the cells to reverse transcribe cellular $V_H$ and $V_L$ mRNA into the corresponding cDNA sequences. Reverse transcription may be performed in a single step or optionally together with a PCR procedure, using a reverse transcriptase, sufficient quantities of the four dNTPs and primers that bind to the mRNA providing a 3' hydroxyl group for reverse transcriptase to initiate polymerization. Any primer complementary to the mRNA may be used, but it is preferred to use primers complementary to the 3'-terminal end of the $V_H$ and $V_L$ molecules so as to facilitate selection of variable region mRNA. Numerous studies have indicated that degenerate oligonucleotides can be prepared to serve as the 5'-end primers for $V_H$ and Vκ or Vλ. The combinatorial library method of making targeting molecules relies on such primers. Furthermore, numerous experiments have shown that PCR can amplify the gene segments of interest, such as $V_H$ and $V_L$, from a single cell. Because of the ability to work with even a single cell, this PCR approach can generate antibodies even where the B cells of interest occur at low frequency.

In the high diversity embodiment, after FACS sorting, the cells of B cell library are pooled and the RT-PCR is performed on the entire pool of cells. Generation of mRNA for cloning antibody purposes is readily accomplished by well-known procedures for preparation and characterization of antibodies (see, e.g., Antibodies: A Laboratory Manual, 1988; incorporated herein by reference). For example, total RNA from the B-cell library is extracted by appropriate methods which are standard and conventional in the art. cDNA is then synthesized from the RNA by appropriate methods, e.g. using random hexamer oligonucleotides or V gene or V-gene family-specific primers. Again these are processes known to persons skilled in the art as explained above. Libraries of nucleic acid molecules derived from B-cell libraries, e.g. a library of RNA or cDNA molecules derived from such B-lymphocytes, may be cloned into expression vectors to form expression libraries. In some embodiments, only the $V_H$ domain derived from the B cell library is amplified to generate a library of $V_H$ domains. A $V_L$ library from another source is used in combination with the $V_H$ library to generate antibodies using methods described herein. Libraries of antibody fragments can be constructed by combining $V_H$ and $V_L$ libraries together in any number of ways as known to the skilled artisan. For example, each library can be created in different vectors, and the vectors recombined in vitro, or in vivo. Alternatively, the libraries may be cloned sequentially into the same vector, or assembled together by PCR and then cloned. PCR assembly can also be used to join $V_H$ and $V_L$ DNAs with DNA encoding a flexible peptide spacer to form single chain Fv (scFv) libraries as described elsewhere herein. In yet another technique, "in cell PCR assembly" is used to combine $V_H$ and $V_L$ genes within lymphocytes by PCR and then clone repertoires of linked genes.

Cloning and Expression of B-Cell Library Genetic Material

"Antibody expression library" or "expression library" as used herein can refer to a collection of molecules (i.e. two or more molecules) at either the nucleic acid or protein level. Thus, this term can refer to a collection of expression vectors which encode a plurality of antibody molecules (i.e. at the nucleic acid level) or can refer to a collection of antibody molecules after they have been expressed in an appropriate expression system (i.e. at the protein level). Alternatively the expression vectors/expression library may be contained in suitable host cells in which they can be expressed. The antibody molecules which are encoded or expressed in the expression libraries of the invention can be in any appropriate format, e.g., may be whole antibody molecules or may be antibody fragments, e.g., single chain antibodies (e.g. scFv antibodies), Fv antibodies, Fab antibodies, Fab'2 fragments, diabodies, etc. The terms "encoding" and "coding for" as is "nucleic acid sequence encoding/coding for" or a "DNA coding sequence of" or a "nucleotide sequence encoding/coding for" a particular enzyme—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases with elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

Antibody molecules identified by, derived from, selected from or obtainable from the antibody expression libraries of the invention form a yet further aspect of the invention. Again these antibody molecules may be proteins or nucleic acids encoding antibody molecules, which nucleic acids may in turn be incorporated into an appropriate expression vector and/or be contained in a suitable host cell.

The cDNA pool is then subjected to a primary PCR reaction with oligonucleotides that hybridize to the IgG constant region of the heavy chain of antibody genes and oligonucleotides that hybridize to the 5' end of the variable heavy chain region of antibody genes. A PCR reaction is also set up for the amplification of the variable light ($V_L$) chain pool of kappa and lambda classes. Such oligonucleotides may be designed based on known and publicly available immunoglobulin gene sequence database information. That is, upon reverse transcription, the resulting cDNA sequences may be amplified by PCR using primers specific for immunoglobulin genes and, in particular, for the terminal regions of the $V_H$ and $V_L$ nucleic acids.

The $V_H$ and $V_L$ sequences can be conveniently obtained from a library of $V_H$ and $V_L$ sequences produced by PCR amplification using V gene family-specific primers or V gene-specific primers (Nicholls et al., J. Immunol. Meth., 1993, 165:81; WO93/12227) or are designed according to standard art-known methods based on available sequence information. (The $V_H$ and $V_L$ sequences can be ligated, usually with an intervening spacer sequence (e.g., encoding an in-frame flexible peptide spacer), forming a cassette encoding a single-chain antibody.) V region sequences can be conveniently cloned as cDNAs or PCR amplification products for immunoglobulin-expressing cells. The $V_H$ and $V_L$ regions are sequenced, optionally, in the methods described herein and particularly after certain steps as noted (e.g., after single cell PCR; after mammalian or other cell surface display, after FACS screening, and the like). Sequencing is used, among other reasons, to verify that the level of diversity is at an acceptable level. Sequencing can include high-throughput sequencing, deep sequencing (in which the same gene is sequenced from a plurality of individual samples to identify differences in the sequences), or combinations of the two.

In some embodiments in which it is desired to maintain the natural $V_H$ and $V_L$ combinations, cDNAs are PCR amplified and linked in the same reaction, using, in addition to the cDNA primers, one primer for the 5' end of the $V_H$ region gene and another for the 5' end of the $V_L$ gene. These primers also contain complementary tails of extra sequence, to allow the self-assembly of the $V_H$ and $V_L$ genes. After PCR amplification and linking, the chance of getting mixed products, in other words, mixed variable regions, is minimal because the amplification and linking reactions were performed within each cell. The risk of mixing can be further decreased by utilizing bulky reagents such as digoxigenin labeled nucleotides to further ensure that V region cDNA pairs do not leave the cellular compartment and intermix, but remain within the cell for PCR amplification and linking. The amplified sequences are linked by hybridization of complementary terminal sequences. After linking, sequences may be recovered from cells for use in further method steps described herein. For example, the recovered DNA can be PCR amplified using terminal primers, if necessary, and cloned into vectors which may be plasmids, phages, cosmids, phagemids, viral vectors or combinations thereof as detailed below. Convenient restriction enzyme sites may be incorporated into the hybridized sequences to facilitate cloning. These vectors may also be saved as a library of linked variable regions for later use.

In some embodiments in which it is desired to provide additional $V_H$ and $V_L$ combinations, the expression system is chosen to facilitate this. For example. bacteriophage expression systems allow for the random recombination of heavy- and light-chain sequences. Other suitable expression systems are known to those skilled in the art.

It should be noted that in the case of $V_H$ and $V_L$ sequences derived from non-humans, in some embodiments, it is preferable to chimerize these sequences with a fully human Fc. As used herein "chimerized" refers to an immunoglobulin, wherein the heavy and light chain variable regions are not of human origin and wherein the constant regions of the heavy and light chains are of human origin. This is effected by amplifying and cloning the variable domains into a human Fc. The human Fc can be part of the vector, or in a separate molecule, and library of Fc's could also be used. In a preferred embodiment the chimerized molecules grown in mammalian cells such as CHO cells, screened with FACS twice to enrich the cell population for cells expressing the antibody of interest. The chimerized antibodies are characterized, either sequenced followed by functional characterization, or direct functional characterization or kinetics. Growth, screening and characterization are described in detail below.

It is important to note that the above described PCR reactions are described for cloning the antibodies in the IgG form. These are preferred as they are generally associated with a more mature immune response and generally exhibit higher affinity than IgM antibodies, thereby making them more desirable for certain therapeutic and diagnostic applications. Clearly, however, oligonucleotides can be designed which will allow the cloning of one or more of the other forms of immunoglobulin molecules, e.g., IgM, IgA, IgE and IgD if desired or appropriate.

It should be noted that in the methods and expression libraries of the invention, once appropriate hosts from which a population of antibody producing cells can be isolated has been identified and the appropriate population of said cells have been isolated at an appropriate time and optionally enriched as described above, the antibody expression libraries need not be generated immediately, providing the genetic material contained in the cells can be kept intact thereby enabling the library to be made at a later date. Thus, for example the cells, a cell lysate, or nucleic acid, e.g., RNA or DNA derived therefrom, can be stored until a later date by appropriate methods, e.g., by freezing, and the expression libraries generated at a later date when desired.

Once the library of expression vectors has been generated, the encoded antibody molecules can then be expressed in an appropriate expression system and screened using appropriate techniques which are well known and documented in the art. Thus the above defined method of the invention may comprise the further steps of expressing the library of expression vectors in an appropriate expression system and screening the expressed library for antibodies with desired properties, as explained in further detail below.

As indicated herein, nucleic acid molecules prepared by the methods of the disclosure which comprise a nucleic acid encoding antibody sequences can include, but are not limited to, those encoding the amino acid sequence of an antibody fragment, by itself, the coding sequence for the entire antibody or a portion thereof, the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

The primary PCR products are then optionally subjected to a secondary PCR reaction with new oligonucleotide sets that hybridize to the 5' and 3' ends of the antibody variable domains V-Heavy, V-light kappa and V-light lambda (as appropriate depending on whether the primary PCR reaction with which the new oligonucleotide sets are used was designed to amplify portions of the heavy or light chain antibody genes). These oligonucleotides advantageously include DNA sequences specific for a defined set of restriction enzymes (i.e. restriction enzyme sites) for subsequent cloning. The selected restriction enzymes must be selected so as not to cut within human antibody V-gene segments. Such oligonucleotides may be designed based on known and publicly available immunoglobulin gene sequence and restriction enzyme database information. However, preferred restriction enzyme sites to be included are NcoI, Hind III, MluI and NotI. The products of such secondary PCR reactions are repertoires of various V-heavy, V-light kappa and V-light lambda antibody fragments/domains. This type of secondary PCR reaction is therefore generally carried out when the expression library format of interest is a scFv or Fv format, wherein only the $V_H$ and $V_L$ domains of an antibody are present.

One of skill in the art will recognize that heavy or light chain Fv or Fab fragments, or single-chain antibodies may also be used with this system. A heavy or light chain can be mutagenized followed by the addition of the complementary chain to the solution. The two chains are then allowed to combine and form a functional antibody fragment. Addition of random non-specific light or heavy chain sequences allows for the production of a combinatorial system to generate a library of diverse members.

Libraries of such repertoires of cloned fragments comprising the variable heavy chain regions, or fragments thereof, and/or variable light chain regions, or fragments thereof, of antibody genes derived from the B lymphocytes of immunochallenged hosts as defined herein form further aspects of the invention. These libraries comprising cloned variable regions may optionally be inserted into expression vectors to form expression libraries.

Alternatively, if desired, the primary and secondary PCR reactions can be set up so as to retain all or part of the constant regions of the various heavy and/or light antibody chains contained in the isolated B cell population. This is desirable when the expression library format is a Fab format, wherein the heavy chain component comprises VH and CH domains and the light chain component comprises $V_L$ and $C_L$ domains. Again, libraries of such cloned fragments comprising all or part of the constant regions of heavy and/or light antibody chains form further aspects of the invention.

These nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

The present invention also provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a nucleic acid library. A "nucleic acid library" is comprised of a vector-based collection of one or more nucleic acid molecules in some embodiments. In other embodiments, a "nucleic acid library" is comprised of a non-vector-based collection of nucleic acid molecules. In yet another embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

The present invention also relates to vectors that include isolated nucleic acid molecules of the present invention, host cells that are genetically engineered with the recombinant vectors, and the production of at least one antibody by recombinant techniques, as is well known in the art. See, e.g., Sambrook, et al., supra; Ausubel, et al., supra, each entirely incorporated herein by reference.

In preparing an expression library, the PCR products generated either from single cells or a pool of cells can be cloned into a plasmid for in vitro transcription/translation or, in some embodiments, the appropriate control elements are included within the PCR product for direct in vitro transcription/translation. In vitro transcription/translation of genes uses cell free extracts to provide the required enzymes, ribosomes and protein factors. The synthesis of proteins is directed by mRNA synthesized from the desired DNA templates. The DNA template must contain the appropriate control elements for the system used including a ribosome binding site and promoter sequence. One of skill in the art would clearly recognize the appropriate required elements for each system. The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression. The term "construct" is used herein to describe a molecule, such as a polynucleotide (e.g., a phytase polynucleotide) that may optionally be chemically bonded to one or more additional molecular moieties, such as a vector, or parts of a vector. In a specific—but by no means limiting—aspect, a nucleotide construct is exemplified by a DNA expression construct suitable for the transformation of a host cell.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Expression vectors suitable for surface display and full length antibody display, described below, are particularly preferred. Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

Again, it is noted that in the natural diversity approach, the nucleic acid molecules correspond to the sequences as found in vivo and which are likely to be functional in antigen binding due to the fact that they are expressed by B lymphocytes in a host in response to a specific immunochallenge. In the high diversity approach, the nucleic acid molecules are generated from the B cell library pool, and thus is it possible to create additional light chain/heavy chain combinations that were not present in vivo.

Amplified sequences can be characterized by DNA sequencing, directly cloned as individual sequences into an expression system, or operably linked so that the heavy and light chain nucleic acid sequences are expressed as one contiguous, in-frame protein. The appropriate variable gene fragments may be cloned into an expression vector so as to generate an expression library. As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

In embodiments which utilize single cell PCR, amplified sequences are directly cloned as individual sequences into an expression system, or operably linked so that the heavy and light chain nucleic acid sequences are expressed as one contiguous, in-frame protein. Additionally, they are characterized by DNA sequencing, including high-throughput sequencing methods.

It will be appreciated however from the discussion above that the methods and expression libraries of the invention are not limited to antibodies in any particular format and that formats can equally be generated, for example Fab fragments, Fab'2 fragments, Fv fragments, diabodies, etc., in accordance with methods which are well known in the art. In addition other types of expression vector can be used. In particular other forms of prokaryotic expression vectors can be used, as well as different types of display vectors such as phage, covalent or ribosomal display vectors.

The main requirement of an expression vector is that it contains all the necessary components required for obtaining expression of the appropriate nucleic acid molecule encoding the polypeptide of interest in the particular expression system chosen. Thus, the expression vectors, as well as the nucleic acid fragments encoding the antibody molecules, may optionally additionally contain other appropriate components, for example origins of replication, inducible promoters for initiating transcription and protein expression, antibiotic resistance genes and markers, general tags, detection tags such as myc tags or reporter molecules, primer binding sites to enable amplification of the constructs by e.g., PCR, or any other desirable sequence elements. Appropriate sources and positioning of such additional components within the library constructs so that they perform their desired function would be well within the normal practice of a skilled person in the art.

After cloning into appropriate expression vectors, the antibody expression library can be transformed into E. coli cells or other appropriate host cells depending on the vector system used. The types of expression systems available to produce antibody molecules include bacterial, yeast, insect and mammalian expression systems, the methods for which are well known in the art. Techniques for the production of single chain antibodies could also be adapted to produce single chain antibodies to the antigen of interest.

Prokaryotic in vitro techniques for protein production were the first to be used (Zubay et al., 1970). Subsequently eukaryotic systems were developed using wheat germ (Roberts, 1973) and rabbit reticulocytes (Pelham, 1976). Several new developments have increased the efficiency of these techniques. Examples include, the development of nuclease deficient strains of E. coli to improve the results using linear DNA templates (Yang, 1980) and treatment of reticulocyte lysates with micrococcal nuclease to lower any background expression from the system.

More recent systems developed for in vitro transcription/translation are based on transcription by phage RNA polymerases including SP6 and SP7 (Krieg, 1987, Studier, 1990). DNA placed under the control of T7 promoter elements can be used as a template for in vitro transcription by T7 RNA polymerase or for complete in vitro transcription/translation with the polymerase added to either a prokaryotic or eukaryotic protein synthesis system. While the methods of the present invention can be used with any in vitro transcription/translation system, the T7 system is preferred for transcription and the use of a prokaryotic translation system is preferred as no capping of the RNA is required.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the antibodies. As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation (e.g., Mg++, Ca++); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the antibodies of the present invention (see, Winnacker, "From Genes to Clones," VCH Publishers, N.Y., N.Y. (1987), which is incorporated herein by reference). Eukaryotic cells are preferred, because a number of suitable host cell lines capable of secreting intact immunoglobulins have been developed in the art, and include the CHO cell lines, various COS cell lines, HeLa cells, myeloma cell lines, transformed B-cells. Expression vectors for these cells can include expression control sequences, such as an origin of replication, a promoter, an enhancer (Queen et al., Immunol. Rev. 1986, 89: 49), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 30 obp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment, lipofection, or electroporation may be used for other cellular hosts. Other methods used to transform mammalian cells include the use of Polybrene, protoplast fusion, liposomes, electroporation, and microinjection (see, generally, Sambrook et al., supra).

Once they have been cloned, the nucleic acid molecules encoding the various portions of antibody molecules, e.g. the heavy chains or light chains of antibodies or portions thereof, e.g., $V_H$ and/or $V_L$ chains, may be further diversified using standard or novel techniques, for example by mutation involving the addition, deletion and/or substitution of one or more nucleotides in a controlled (e.g., site directed mutagenesis, comprehensive positional evolution (CPE), and/or comprehensive protein synthesis (CPS) as described herein) or random manner, or by domain swapping, cassette mutagenesis, chain shuffling etc. Synthetic nucleotides may be used in the generation of the diverse nucleic acid sequences. Thus, all or part of the nucleic acids encoding the antibody domains can be synthesized chemically. Preferably however the isolated nucleic acid molecules encoding the various antibody domains for making up the expression library are not subject to further diversification at this stage.

Biological Display of Selected Recombinant Antibodies

Some preferred embodiments utilize a biological display system or mammalian cell surface display system. The term "biological display" refers to a technique whereby a protein or antibody, or a portion of an antibody, is expressed and displayed on a mammalian, bacterial, or yeast host cell surface for screening purposes; for example, by screening for specific antigen binding by a combination of magnetic beads and fluorescence-activated cell sorting. In one aspect, mammalian expression vectors are used for simultaneous expression of immunoglobulins as both a secreted and cell surface bound form as in DuBridge et al., US 2009/0136950, which is incorporated herein by reference. In another aspect, the techniques of Gao et al. are employed for a viral vector encoding a library of antibodies or antibody fragments are displayed on the cell membranes when expressed in a cell as in Gao et al., US 2007/0111260, incorporated herein by reference. Whole IgG surface display on mammalian cells is known. For example, Akamatsuu et al. developed a mammalian cell surface display vector, suitable for directly isolating IgG molecules based on their antigen-binding affinity and biological activity. Using an Epstein-Barr virus-derived episomal vector, antibody libraries were displayed as whole IgG molecules on the cell surface and screened for specific antigen binding by a combination of magnetic beads and fluorescence-activated cell sorting. Plasmids encoding antibodies with desired binding characteristics were recovered from sorted cells and converted to the form for production of soluble IgG. Akamatsuu, et al., J. Immunol. Methods 2007 327(1-2):40-52; incorporated herein by reference. Ho et al. used human embryonic kidney 293T cells that are widely used for transient protein expression for cell surface display of single-chain Fv antibodies for affinity maturation. Cells expressing a rare mutant antibody with higher affinity were enriched 240-fold by a single-pass cell sorting from a large excess of cells expressing WT antibody with a slightly lower affinity. Furthermore, a highly enriched mutant was obtained with increased binding affinity for CD22 after a single selection of a combinatory library randomizing an intrinsic antibody hotspot. Ho et al. Isolation of anti-CD22 Fv with high affinity by Fv display on human cells, Proc Natl Acad Sci USA 2006 Jun. 20; 103(25): 9637-9642; incorporated herein by reference.

Beerli et al. used B cells specific for an antigen of interest which were directly isolated from peripheral blood mononuclear cells (PBMC) of human donors. Recombinant, antigen-specific single-chain Fv (scFv) libraries are generated from this pool of B cells and screened by mammalian cell surface display by using a Sindbis virus expression system. This method allows isolating antigen-specific antibodies by a single round of FACS. The variable regions (VRs) of the heavy chains (HCs) and light chains (LCs) were isolated from positive clones and recombinant fully human antibodies produced as whole IgG or Fab fragments. In this manner, several hypermutated high-affinity antibodies binding the Qβ virus like particle (VLP), a model viral antigen, as well as antibodies specific for nicotine were isolated. All antibodies showed high expression levels in cell culture. The human nicotine-specific mAbs were validated preclinically in a mouse model. Beerli et al., Isolation of human monoclonal antibodies by mammalian cell display, Proc Natl Acad Sci USA. 2008 Sep. 23; 105(38): 14336-14341; incorporated herein by reference.

Yeast cell surface display is also known, for example, see Kondo and Ueda 2004, Yeast cell-surface display-applications of molecular display, Appl. Microbiol. Biotechnol., 64(1): 28-40, which describes for example, a cell-surface engineering system using the yeast *Saccharomyces cerevi-*

*siae*. Several representative display systems for the expression in yeast *S. cerevisiae* are described in Lee et al., 2003, Microbial cell-surface display, TRENDS in Biotechnol. 21(1): 45-52. Also Boder and Wittrup 1997, Yeast surface display for screening combinatorial polypeptide libraries, Nature Biotechnol., 15(6):553. Pakabunto K, Xu Z, Zhang Y, Tsurushita N.

In preferred embodiments, full-length antibodies are displayed in cell surface display systems. Whole antibody cell surface display systems have been developed for some eukaryotic cells, such as yeast (see, e.g., Boder and Wittrup, 2000, Methods in Enzymology, 328:430-444). In more preferred embodiments, full-length antibodies are displayed in mammalian cell surface display systems. Full-length antibody mammalian cell surface display systems are known in the art, for example: Akamatsu, et al., Whole IgG surface display on mammalian cells: Application to isolation of neutralizing chicken monoclonal anti-IL-12 antibodies. J Immunol Methods. 2007 Oct. 31; 327(1-2):40-52.; U.S. Pat. Nos. 7,790,655; 7,732,195; Zhou, et al., Development of a novel mammalian cell surface antibody display platform. MAbs. 2010 September-October; 2(5):508-18. In the method of the present invention, such mammalian expression systems, in particular systems using cell surface display of molecules for screening and selection, are employed to identify and select candidates for manufacturing, or evolution followed by manufacturing. Preferably, such mammalian hosts are Fibroblast cells (3T3, mouse; BHK21, Syrian hamster) Epithelial cells (MDCK, dog; Hela, human; PtK1, rat kangaroo) Plasma cells ((SP2/0 and NS0, mouse) Kidney cells (293, human; COS, monkey) Ovary cells (CHO, Chinese hamster) Embryonic cells (R1 and E14.1, mouse; H1 and H9, human; PER C.6, human) Cell surface display technology is employed to display proteins on the surface of the mammalian cells for screening. Proteins are cloned as fusions with membrane molecules which when expressed display the proteins on the surface of the cells for rapid, high-throughput screening, for example. Such fusion proteins are known to those skill in the art. For example WO 10/094027, incorporated by reference herein in its entirety, describes one type of fusion protein which is suitable for use in biological display systems described herein.

Recombinant host cells displaying expressed immunoglobulins can be screened for desired binding activity using affinity-based enrichment assays. In some embodiments, recombinant host cells displaying immunoglobulins are screened for immunoglobulins that bind specifically to a target antigen of interest, via assays that include, but are not limited to fluorescence-activated cell sorting (FACS), bead-based sorting such as magnetic bead-based sorting (MACS), or other solid phase panning techniques. ELISA assays can also be performed on immunoglobulins or immunoglobulins displayed on the cell membrane. See, also, Harlow & Lane, Antibodies, A Laboratory Manual (1988), for a description of immunoassay formats and conditions that can be used to determine specific immunoreactivity. Optionally, sequencing can be performed before the FACS screening step, after the FACS screening step, or both.

Characterization of Selected Recombinant Antibodies

Once expressed, the antibodies produced are subjected to further screening, binding confirmation, high throughput kinetics, functional characterization, and optionally, sequencing in order to provide recombinant monoclonal antibodies with desired properties. Beyond mere synthesis, antibodies may be characterized according to various properties and an extensive range of functions. Properties include isoelectric point, thermal stability, sedimentation rate, rigidity/flexibility, shape, charge, stability in different pH, solvent, UV, mechanical, and sonic conditions, half life, glycosylation, folding and/or other properties under varying conditions. One manner of examining folding is the ability to be recognized by a cognate binding partner. A wide variety of different immunoassay formats are available for this purpose and are well known in the art. Principally, changes in either affinity or specificity can be determined when the protein is contacted with a specific target or panels of related ligands.

Thermal Stability. Thermal stability of the compositions of the invention may be analyzed using a number of non-limiting biophysical or biochemical techniques known in the art. In certain embodiments, thermal stability is evaluated by analytical spectroscopy. An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the protein unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of lefthanded polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol, 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

In other embodiments, the thermal stability of a composition of the invention is measured biochemically. An exemplary biochemical method for assessing thermal stability is a thermal challenge assay. In a "thermal challenge assay", a composition of the invention is subjected to a range of elevated temperatures for a set period of time. For example, in one embodiment, test molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide of the invention) the binding activity of the binding protein may be determined by a functional or quantitative ELISA.

In certain embodiments, thermal stability is evaluated by measuring the melting temperature (Tm) of a composition of the invention using any of the above techniques (e.g. analytical spectroscopy techniques). The melting temperature is the temperature at the midpoint of a thermal transition curve wherein 50% of molecules of a composition are in a folded state.

In other embodiments, thermal stability is evaluated by measuring the specific heat or heat capacity (Cp) of a composition of the invention using an analytical calorimetric technique (e.g. DSC). The specific heat of a composition is the energy (e.g. in kcal/mol) required to raise by 1° C., the temperature of 1 mol of water. As large Cp is a hallmark of a denatured or inactive protein composition. In certain embodiments, the change in heat capacity (ACp) of a composition is measured by determining the specific heat of a composition before and after its thermal transition. In other embodiments, thermal stability may be evaluated by measuring or determining other parameters of thermodynamic stability including Gibbs free energy of unfolding (AG), enthalpy of unfolding (AH), or entropy of unfolding (AS).

In other embodiments, one or more of the above biochemical assays (e.g. a thermal challenge assay) is used to determine the temperature (ie. the Tc value) at which 50% of the composition retains its activity (e.g. binding activity).

The isoelectric point (pI), sometimes abbreviated to IEP, is the pH at which a particular molecule or surface carries no net electrical charge. Antibodies can be separated according to their isoelectric point (overall charge) on a polyacrylamide gel using a technique called isoelectric focusing, which uses a pH gradient to separate proteins.

Sedimentation rat is an analytical method that measures the rate at which molecules move in response to centrifugal force generated in a centrifuge. This sedimentation rate provides information about both the molecular mass and the shape of molecules. In some cases this technique can also measure diffusion coefficients and molecular mass.

Antibody folding may be determined directly, or in relative terms, inferred from other parameters such as solubility and yield. E.g., an increased yield may reflect an increased folding efficiency.

Neutralization of antibody activity refers to the ability of an antibody to defend a cell from an antigen or infectious body by inhibiting or neutralizing any effect it has biologically. Determination of neutralizing activity is dependent on the particular antigen and suitable assays will be apparent to the skilled artisan.

Determination of antagonistic activity refers to the ability of an antibody to bind to a receptor, blocking or dampening agonist-mediated responses, but not provoking a biological response itself. Determination of antagonistic activity is dependent on the particular receptor and suitable assays will be apparent to the skilled artisan.

Determination of agonistic activity refers to the ability of an antibody to bind to a receptor, triggering a biological response. Determination of agonistic activity is dependent on the particular receptor and suitable assays will be apparent to the skilled artisan.

Antibody expression levels can be determined by any number of known methods. In the PCR in combination with prior reverse transcription (RT-PCR) of the mRNA of interest provides a means for measuring gene expression using as few as one cell when utilized with detectable labels.

Immunoassays can be generally divided into two types: heterogeneous assays requiring multiple separation steps, and homogeneous assays which are performed directly. Heterogeneous immunoassays in general involve a ligand or antibody immobilized on a solid matrix. A sample containing a ligand is contacted with the immobilized antibody and the amount of complex formed on the matrix support is determined from a label attached directly or indirectly to the immobilized complex. As used in the context of the present invention, ligand is defined as a species that interacts with a non-identical molecule to form a tightly bound, stable complex. The ligand is preferably the target antigen or an immunogenic portion thereof. For practical purposes, the binding affinity is usually greater than about $10^6$ $M^{-1}$, preferably with an affinity of about at least $5 \times 10^7$ $M^{-1}$ more preferably with an affinity of at least $1\times10^8$ $M^{-1}$ to $1\times10^9$ $M^{-1}$ or more, sometimes up to $1\times10^{10}M^{-1}$-$10^{15}$ $M^{-1}$.

Heterogeneous immunoassays may be performed as sandwich assays in which a molecule of interest is reacted with an immobilized antibody that specifically binds that molecule with high affinity. In a second step, a conjugate formed from the same or different antibody to the antigen and a marker molecule is reacted with the antigen-antibody complex on the immobilization matrix. After removal of excess free marker conjugate, the bound marker conjugate, which is proportional to the amount of ligand in the sample, is measured.

Detection of immunocomplex formation is well known in the art and may be achieved through the application of numerous approaches. These approaches are typically based upon the detection of a label or marker, such as any of the radioactive, fluorescent, chemiluminescent, electrochemiluminescent, biological or enzymatic tags or labels known in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Preferred methods for detection include radioimmunoassay (RIA) or enzyme-linked immunosorbent assay (ELISA) with ELISA being most preferred due to generally increased sensitivity. ELISAs are extensively used in biotechnology applications, particularly as immunoassays for a wide range of antigenic substances. The sensitivity of ELISA is based on the enzymatic amplification of the signal. Other techniques include western blots, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel, et al, eds, 1994, Current Protocols in Molecular Biology, Vol. 1, John Wiley & Sons, Inc., New York, which is incorporated by reference herein in its entirety).

Screening for a functional activity such as neutralization of antigen activity, or antagonistic or agonistic activities can also be performed, having high antigen binding affinity or being able to inhibit enzymatic activity. Such assays are known in the art, for example, functional screening of receptor/ligand binding. Antibodies may be selected based on binding affinities such as, for example, may be determined using a BIAcore™ machine, or using a competitive radioimmunoassay. Thus, the antibody expression library is generally screened for antibody molecules which interact with a particular target antigen, e.g., the target antigen with which the original immunization was performed, and to which the initial B cell library bound. Once one or more antibody molecules identified using the methods of the invention (or the nucleic acid encoding them) can be isolated and purified. Other desirable properties to determine include determining expression level, determining non-specific binding, and determining specificity.

Thus, a further aspect of the present invention provides a method of identifying and/or isolating one or more antibody molecules exhibiting desired properties from an antibody expression library as defined herein, said method comprising the step of screening an antibody expression library of the invention for molecules which display certain properties. A preferred aspect of the invention thus provides a method of identifying and/or isolating from an antibody expression library as defined herein one or more antibody molecules which is a specific binding partner for a target antigen, the method comprising the steps of a) screening an expression library of the invention for antibody molecules which bind to a particular target antigen and b) identifying and/or isolating the relevant library member.

Once an antibody library member is identified, it may optionally be subjected to further manipulation, such as humanization, screening for additional functionalities, evolution, and/or engineering.

In one embodiment, the antibody can be humanized Humanization by CDR grafting, or reshaping, involves intercalating the mouse CDRs from each immunoglobulin chain within the FW regions of a human variable region. One method of CDR grafting can be used to create what is called termed framework-patched immunoglobulins and is disclosed in Leung et al., U.S. Pat. No. 7,321,026, which is incorporated herein by reference. Unlike previous described methods of humanization, which grafted CDRs from a donor onto the frameworks of a single acceptor immunoglobulin, segments of framework (FR1, FR2, FR3, and FR4), or FRs, were patched to replace the corresponding FRs of the parent immunoglobulin. Free assortment of these FRs from different immunoglobulins and from different species was mixed and matched into forming the final immunoglobulin chain. Immunoglobulin chains were prepared utilizing one or more complementarity determining regions (CDR's) from a donor immunoglobulin and portions of framework sequences from one or more human, or primate immunoglobulins. The individual FR sequences are selected by the best homology between the non-human antibody and the human antibody template. This approach, however, is labor intensive, and the optimal framework regions are not easily identified.

Another method of CDR grafting is described by Williams et al. in Antibody Engineering, Vol. 1, Chapter 21, Konterman and Dubel, (eds.), Springer-Verlag Berlin Heidelberg 2010, pp. 319. FR sequences are selected by the best homology between the non-human antibody and the human antibody template. Selection of the human variable regions is considered to be of critical importance. There are over 9,000 heavy and over 2,500 kappa antibodies in the public databases. These include Kabat, GenBank, and IMGT databases. By aligning these databases with the Kabat numbering system and introducing gaps where necessary, each human variable region is scored for identity to the mouse sequence. The residue identity is determined at FW region, canonical, VH-VK interface residues and residues are identified from the homology models of potential importance. In addition, N-glycosylation patterns in the FW region are identified, which may lead to glycosylation-dependent effects on antibody binding. The resulting human variable region sequences are refined by maximizing sequence identity and homology to the mouse antibody.

The typical CDR grafting strategy described by Williams et al. 2010 starts with cloning and sequencing variable region cDNAs from a mouse B cell hybridoma. Chimeric heavy and light chain constructs are prepared utilizing the cDNA sequences. CDR grafted human variable regions are designed in parallel and CDR grafted humanized heavy and light chain constructs are prepared. Recombinant antibodies are expressed in transient transfection using chimeric and/or humanized expression constructs. The antigen binding potency of recombinant humanized antibodies is tested. If potency is low, further humanized antibody versions are prepared by substituting with selected framework mouse residues. The goal is to obtain a humanized antibody with optimum antigen binding potency, but with minimum mouse framework region antibodies. This process of humanization by CDR grafting is also somewhat labor intensive, potentially requiring multiple iterations to prepare a humanized antibody exhibiting the most desirable characteristics.

Another method of humanizing antibodies which also involves reshaping to reduce the immunogenicity involves synthesizing a combinatorial library comprising CDRs from a donor antibody fused in frame to framework regions from a sub-bank of framework regions. This technique, called framework-shuffling of antibodies, is disclosed in Wu et al US 2010/0216975, which is incorporated herein by reference. For example, Wu et al. prepared combinatorial sub-libraries that were assembled sequentially using the polymerase chain reaction (PCR) by overlap extension.

Another technique of express humanization of antibodies with reduced immunogenicity; while maintaining or increasing antigen-binding specificity and affinity when compared to the donor antibody, and simultaneously optimizing protein expression is disclosed in U.S. Patent Application No. 61/428,917 filed Dec. 31, 2010, hereby incorporated by reference. Briefly, a method of producing humanized antibodies from a template antibody in which the variable region or CDRs are derived from the template antibody and the framework and constant regions of the antibody are derived from one or more human antibodies is disclosed. In one aspect, the frameworks are from a human framework pool of functionally expressed human antibodies. In another aspect, a single sequence is utilized for framework region 4 in either or both of the light chain and the heavy chain. In a further aspect, the sequence encoding framework 4 is comprised in the expression vector. The variable region or CDRs derived from the template antibody preferably have from about 90% to about 100% identity with the variable region or CDRs of the template antibody, although any and all modifications, including substitutions, insertions and deletions, are contemplated so long as the humanized antibody maintains the ability to bind to the target antigen.

The antibody expression libraries of the invention and selected antibodies can be screened against other antigens, as well as the target antigen to determine specificity. For example, the libraries of the invention can be screened against antigens similar to the target antigen either to avoid or to obtain cross-reactive antibodies. For example in the course of generating antibodies against infectious diseases the libraries can be screened against different strains of the disease-causing agent. Antibodies specific for one strain may recognize a disease specific antigen. Conversely, antibodies binding different strains can recognize common antigens among the strains. At least the antibodies must recognize common or structurally similar epitopes on antigens. Such antibodies, identified by screening the libraries of the invention with two or more different but related target antigens, e.g., target antigens from different strains of a particular infectious agent (i.e., antibodies identified by differential screening) are particularly good candidates for use as therapeutic or prophylactic antibodies against a specific strain or different strains of a disease causing agent and form a preferred embodiment of the invention.

In one embodiment, the antibody can be evolved using Comprehensive Positional Evolution (CPE). CPE is described in U.S. Patent Application Ser. No. 61/365,216, filed Jul. 16, 2010, entitled Novel Methods of Protein Evolution. U.S. Patent Application Ser. No. 61/365,216 is incorporated by reference in its entirety.

Briefly, using a linear peptide as a simple example, in a first step, a set of naturally occurring amino acid variants (or a subset thereof, or amino acid derivatives) for each codon from position 1 to n (n corresponding to the number of residues in the polypeptide chain) is generated. This procedure is repeated for each polypeptide chain of the target molecule. A minimum set of amino acid mutations contains only one codon for each of the 19 natural amino acids. However, it is recognized that each expression system may suffer from codon bias, in which insufficient tRNA pools can lead to translation stalling, premature translation termination, translation frameshifting and amino acid misincorporation. Therefore, for expression optimization each set contains up to 63 different codons, including stop codons. In the next step, the mutations are confirmed by sequencing each new molecule. Other methods of confirmation can also be employed.

Each amino acid set is then screened for at least one of:
Improved function
Neutral mutations
Inhibitory mutations
Expression
Compatibility of the clone with the host system.

In one aspect, multiple characteristics are screened for simultaneously such as, for example, improved function and expression.

The data for each set are combined for the entire polypeptide chain(s) and a detailed functional map (referred to herein as an EvoMap™) of the target molecule is generated. This map contains detailed information how each mutation affects the performance/expression and/or cloning capability of the target molecule. It allows for the identification of all sites where no changes can be made without a loss in protein function (or antigen/receptor binding in case of antibodies). It also shows where changes can be made without affecting function. The map further identifies changes that result in molecules that do not express in the host system, and therefore do not assess the effect of the mutation.

In the EvoMap™, each position on the template is identified as a restricted site (non-mutable), a fully mutable site, a partially mutable site or an up-mutant for a specific amino acid substitution. Each partially mutable site may be further designated as amenable to substitution with, for example, a charged residue, or a non-polar residue substitution, and a non-expressing clone and/or molecule that cannot be cloned in the host system.

It is possible to utilize the EvoMap™ in order to recognize and recombine beneficial single amino acid substitutions, and screen to further optimize the desired characteristics in the target molecule. However, evolution of certain characteristics may require two or more simultaneous mutations to become observable. The EvoMap™ may be exploited to efficiently, and cost effectively, produce a set of multi-site mutant polypeptides in a non-random fashion. The set of multi-site mutant polypeptides can then be screened for multi-site upmutants.

CPE enables the complete in vivo confirmed protein mutation map. Identification of the entire set of up-mutants enables further combinatorial evolution step(s). CPE can be utilized in order to reduce the immunogenicity risk of evolved proteins by the selection of non-surface mutations; elimination of T-cell epitopes; and mimicry of somatic mutations.

In one aspect, CPE can be used to generate a library of up to 5, 10 or 15 amino acids, or up to all 19 amino acids. Changes are made at each position in the protein and screened for a desirable characteristic, such as binding affinity or expression, and the Evomap™ is created. Later rounds of mutation and screening can be used to generate the data for all 19 amino acids. From the map, fully mutable sites are identified. These sites are useful to identify positions that can be modified to create a new collection of molecules that can be made and tested for new characteristics. For example, informatics can be employed to identify HLA haplotypes in the sequence, and desired changes can be made to avoid these haplotypes by making specific targeted changes at "neutral" ("fully mutable") sites identified from the map, where the primary characteristic will not be affected. This could potentially reduce immunogenicity risk (one could select non-surface mutations, eliminate t-cell epitopes, mimic hypersomatic mutations). Further, the map can show sites for site specific modifications (glycosylation and chemical conjugation) to improve various characteristics. Also, optimization of silent mutations can improve protein expression in a variety of hosts.

Combinatorial Protein Synthesis (CPS™) involves combining individual hits from CPE, CPI, CPD, or any other evolutionary technique to combine two or more mutations. CPS is used to synthesize proteins with combined mutations which are then screened for optimized gene and protein characteristics. In one aspect, two or more point mutations which result in up-mutants or neutral mutations are combined in CPS. CPS is described in U.S. Patent Application Ser. No. 61/365,216, filed Jul. 16, 2010.

In one embodiment CPE is combined with CPS to create mutants, which are screened for the desired property. In one aspect, time and resources can be saved in the CPE process by changing 2 aa or 3 aa or 4 aas at a time versus one at a time; so if the number of aa's in the protein is N, the total number generated and screened for 2 aa at a time would be $(20^2) \times \frac{1}{2}N$; 3 at a time would be $(20^3) \times \frac{1}{3}N$, etc. For example, in one specific aspect, (in the 2 aa example): $1^{st}$ aa at $1^{st}$ aa position is combined with all 20 at the $2^{nd}$ aa position and all the other aa's remain the same, then the $2^{nd}$ aa at $1^{st}$ aa position is combined with all 20 at the $2^{nd}$ aa position and all other aa's remain the same. The entire population is screened for up mutants and then mutation at the second set of the next two aa's down the line is performed. In a similar aspect, this can be performed for 3 aas at a time or 4 aas at a time. In another aspect, the CPE process is followed by CPS of up-mutants (including any subset thereof).

When one or more antibody molecule candidates have been selected, identified, humanized, evolved, engineered and/or purified using the methods and expression libraries of the invention, these candidates, or a component, fragment, variant, or derivative thereof may be manufactured and if desired formulated with at least one pharmaceutically acceptable carrier or excipient. Such manufactured antibody molecules, or components, fragments, variants, or derivatives thereof, are also encompassed by the present invention. Alternatively, these antibody molecules may take the form of nucleic acids encoding antibody molecules, which nucleic acids may in turn be incorporated into an appropriate expression vector and/or be contained in a suitable host cell. Thus, nucleic acid molecules encoding said antibody molecules, or expression vectors containing said nucleic acid molecules form further aspects of the invention.

Once a particular antibody molecule, or a component, fragment, variant, or derivative thereof, has been selected, identified, etc., in accordance with the present invention, the expression vector encoding the selected antibody can readily be used (or adapted for use) to produce sufficient quantities of the antibody molecule by expression in appropriate host cells or systems and isolating the antibody molecules from the host cell or system or from the growth medium or supernatant thereof, as appropriate. Alternatively, said antibody molecules may be produced by other appropriate methods, e.g., by chemical synthesis of the nucleic acid encoding the antibody and expression in a suitable host or in an in vitro transcription system.

Thus, a yet further aspect of the invention provides a method of manufacturing a specific antibody molecule comprising the steps of identifying a specific antibody molecule which is a binding partner for a target antigen according to the methods of the invention as described above, manufacturing said identified antibody molecule, or a component, fragment, variant, or derivative thereof and optionally formulating said manufactured antibody molecule with at least one pharmaceutically acceptable carrier or excipient. Antibody molecules (or components, fragments, variants, or derivatives thereof), identified, manufactured or formulated in this way form yet further aspects of the invention. The main requirement for such components, fragments, variants, or derivative antibody molecules is that they retain their original functional activity in terms of ability to bind a specific antigen or have improved functional activity.

In one embodiment, the selected antibody is generated, evolved, and expressed in a eukaryotic host, such as a mammalian cell host or a yeast cell host, for manufacturing in a single system, The system of Comprehensive Integrated Antibody Optimization (CIAO™) which allows for simultaneous evolution of protein performance and expression optimization. CIAO!™ is disclosed International Patent Application Ser. No PCT/US2010/42302, filed Jul. 16, 2010, and incorporated herein by reference in its entirety.

In one embodiment the disclosure provides a method of selection, evolution and expression of an antibody in a mammalian cell production host; the method comprising generating an anti-antigen antibody library in a mammalian cell production host with antibody cell surface display; screening the library for at least one predetermined property, characteristic or activity; selecting a template antibody from the library; evolving the template antibody to produce a set of mutant antibodies in the mammalian cell production host with antibody cell surface display; screening the mutant antibodies for the at least one predetermined property, characteristic or activity; selecting an up-mutant antibody from the set of mutant antibodies based upon optimization of the at least one predetermined property, characteristic or activity when compared to the template antibody; and expressing the up-mutant antibody in the same mammalian cell production host as used in the generating step. In one aspect, the antigen is pre-selected. In another aspect, the anti-antigen antibody library is a humanized anti-antigen antibody library.

What is claimed is:

1. A method of generating a recombinant antibody that binds at least one target antigen comprising:
   a) amplifying cDNA obtained from mRNA of B cells from a non-human host selected from a rabbit, a mouse, a rat, a hamster, a guinea pig, and a goat, which are capable of binding to the at least one target antigen to prepare an immunoglobulin library comprising cDNA encoding $V_H$ and $V_L$ domains;
   b) generating antibodies from the $V_H$ and $V_L$ domains whereby the antibodies comprise light and heavy chain combinations;
   c) screening the antibodies with the at least one target antigen to identify a subset of antibodies capable of binding to the at least one target antigen; and
   d) humanizing at least one antibody of the subset of antibodies to generate the recombinant antibody, whereby a recombinant antibody that binds at least one target antigen is generated.

2. The method of claim 1, further comprising a step of providing a B cell library and wherein the number of combinations generated in step b is more than the number of B cells in the B cell library and the B cell library contains at least $10^3$ B cells.

3. The method of claim 1, wherein the a) screening is selected from the group consisting of fluorescence activated cell sorting (FACS) and panning.

4. The method of claim 1, wherein the at least one target antigen is a single target antigen.

5. The method of claim 2, wherein the at least one target antigen is at least two target antigens and the a) screening is screening for B cells capable of binding to the at least two target antigens.

6. The method of claim 5, wherein the at least two target antigens are two epitopes on a single target molecule.

7. The method of claim 1, wherein the non-human host is immunized with a target antigen.

8. The method of claim 1, wherein the antibodies generated in step b) are full length antibodies, antibody fragments, antibody derivatives, fusion proteins, or chimerized antibodies.

9. The method of claim 8, wherein the antibodies are chimerized antibodies that comprise a human Fc.

10. The method of claim 1, wherein the generating employs a biological display system to obtain a cell population displaying the antibodies.

11. The method of claim 10, wherein c) is screening the cell population via fluorescence activated cell sorting (FACS).

12. The method of claim 10, wherein the biological display system is a mammalian cell surface display system or a yeast cell surface display system.

13. The method of claim 1, further comprising, after step b), obtaining the DNA sequence encoding $V_H$ and $V_L$ domains.

14. The method of claim 1, further comprising, after step cd), obtaining the DNA sequence encoding $V_H$ and $V_L$ domains.

15. The method of claim 13, further comprising after step d), obtaining the DNA sequence encoding $V_H$ and $V_L$ domains by a method selected from the group consisting of high-throughput sequencing, deep sequencing and combinations of the foregoing.

16. The method of claim 2, wherein the B cell library is provided by a high-throughput screening of B cells from the non-human host.

17. The method of claim 1, wherein the screening step d) is a high-throughput screening.

18. The method of claim 17, wherein the high-throughput screening is via FACS or a screening an array.

19. The method of claim 1, further comprising:
e) characterizing the antibodies capable of binding to the at least one target antigen.

20. The method of claim 19, wherein step e) comprises performing a binding assay to determine binding affinity to the target antigen.

21. The method of claim 20, wherein the binding assay comprises an ELISA.

22. The method of claim 20, wherein the binding affinity to the at least one target antigen is greater than 10 μM.

23. The method of claim 1, wherein step a_) comprises RT-PCR.

24. The method of claim 19, wherein step e) comprises characterizing selected from the group consisting of determining isoelectric point, determining thermal stability, determining sedimentation rate, determining folding rate, determining neutralization of antigen activity, determining antagonistic activity, determining agonistic activity, determining expression level, determining non-specific binding, determining specificity, and determining inhibition of enzymatic activity, determining rigidity/flexibility, determining shape, determining charge, determining stability in different pH, determining stability in different solvents, determining UV stability, determining stability in different mechanical conditions, determining stability in different sonic conditions, determining half life, and determining glycosylation.

25. The method of claim 1, further comprising evolving the recombinant antibody.

26. The method of claim 25, where the evolving is selected from the group consisting of Comprehensive Positional Evolution, Comprehensive Positional Evolution followed by Comprehensive Protein Synthesis, random mutagenesis, and PCR shuffling.

27. The method of claim 1, wherein the humanizing step comprises CDR grafting.

28. The method of claim 27, wherein the CDR grafting comprises intercalating CDRs of the least one antibody of step d within the framework regions of human antibody.

29. The method of claim 1, wherein the humanizing step comprises synthesizing a combinatorial library comprising CDRs of the least one antibody of step d fused in frame to framework regions from a sub-bank of framework regions.

30. The method of claim 1, wherein the humanizing step comprises fusing variable region or CDRs of the least one antibody of step d with constant regions or framework regions derived from one or more human antibodies.

31. The method of claim 1, further comprises screening evolved recombinant antibodies for a recombinant antibody with an additional functionality selected from neutralization of antigen activity, antagonistic activity, agonistic activity, inhibition of enzymatic activity, and having a high antigen binding affinity.

* * * * *